United States Patent
Banchereau et al.

(10) Patent No.: US 8,481,314 B2
(45) Date of Patent: Jul. 9, 2013

(54) ACTIVATION OF HUMAN ANTIGEN-PRESENTING CELLS THROUGH DENDRITIC CELL LECTIN-LIKE OXIDIZED LDL RECEPTOR-1 (LOX-1)

(75) Inventors: Jacques F. Banchereau, Dallas, TX (US); SangKon Oh, Baltimore, MD (US); Gerard Zurawski, Midlothian, TX (US); Sandra Zurawski, Midlothian, TX (US); Dapeng Li, Dallas, TX (US)

(73) Assignee: Baylor Research Institute, Dallas, TX (US)

( * ) Notice: Subject to any disclaimer, the term of this patent is extended or adjusted under 35 U.S.C. 154(b) by 1083 days.

(21) Appl. No.: 12/036,138

(22) Filed: Feb. 22, 2008

(65) Prior Publication Data

US 2008/0267984 A1 Oct. 30, 2008

Related U.S. Application Data

(60) Provisional application No. 60/891,424, filed on Feb. 23, 2007.

(51) Int. Cl.
*C12N 5/071* (2010.01)
*C07K 16/00* (2006.01)
*C12P 21/08* (2006.01)

(52) U.S. Cl.
USPC ...................................... 435/372; 530/388.7

(58) Field of Classification Search
None
See application file for complete search history.

(56) References Cited

U.S. PATENT DOCUMENTS

| | | | |
|---|---|---|---|
| 3,791,932 | A | 2/1974 | Schuurs et al. |
| 3,949,064 | A | 4/1976 | Bornstein et al. |
| 4,174,384 | A | 11/1979 | Ullman et al. |
| 4,554,101 | A | 11/1985 | Hopp |
| 5,945,308 | A | 8/1999 | Tang et al. |
| 6,541,011 | B2 | 4/2003 | Punnonen et al. |
| 7,129,039 | B2 | 10/2006 | Ariizumi et al. |
| 2004/0258688 | A1 | 12/2004 | Hawiger et al. |
| 2006/0269949 | A1 | 11/2006 | Halloran |

OTHER PUBLICATIONS

Luft et al., 2002, Int. Immunol. vol. 14: 367-380.*
Balazs, M., et al., "Blood dendritic cells interact with splenic marginal zone B cells to initiate T-independent immune responses." Immunity (2002), 17:341-352.
Banchereau, J., et al., "Immunobiology of dendritic cells." Annu Rev Immunol (2000), 18:767-811.
Bates, E E., et al., "APCs express DCIR, a novel C-type lectin surface receptor containing an immunoreceptor tyrosine-based inhibitory motif." J Immunol (1999), 163:1973-1983.
Bendtsen, J. D., et al., "Improved prediction of signal peptides: SignalP 3.0." J Mol Biol (2004), 340:783-795.
Bergtold, A., et al., "Cell surface recycling of internalized antigen permits dendritic cell priming of B cells." Immunity (2005), 23:503-514.
Bernasconi, N. L., et al., "Maintenance of serological memory by polyclonal activation of human memory B cells." Science (2002), 298:2199-2202.
Brown, G. D. "Dectin-1: a signalling non-TLR pattern-recognition receptor." Nat Rev Immunol (2006), 6:33-43.
Cambi, A., et al., "The C-type lectin DC-SIGN (CD209) is an antigen-uptake receptor for *Candida albicans* on dendritic cells." Eur J Immunol (2003), 33:532-538.
Cooper, A. M., et al., "Mice lacking bioactive IL-12 can generate protective, antigen-specific cellular responses to mycobacterial infection only if the IL-12 p40 subunit is present." J Immunol (2002), 168:1322-1327.
Craxton, A., et al., "Macrophage- and dendritic cell—dependent regulation of human B-cell proliferation requires the TNF family ligand BAFF." Blood (2003), 101:4464-4471.
Deineste, Y., et al., "Involvement of LOX-1 in dendritic cell-mediated antigen cross-presentation." Immunity (2002) 17:353-362.
D'Ostiani, C. F., et al., "Dendritic cells discriminate between yeasts and hyphae of the fungus *Candida albicans*. Implications for initiation of T helper cell immunity in vitro and in vivo." J Exp Med (2000), 191:1661-1674.
Dubois, B., et al., "Dendritic cells directly modulate B cell growth and differentiation." J Leukoc Biol (1999), 66:224-230.
Figdor, C. G., et al., "C-type lectin receptors on dendritic cells and Langerhans cells." Nat Rev Immunol (2002), 2:77-84.
Fradin, C., et al., "beta-1,2-linked oligomannosides from *Candida albicans* bind to a 32-kilodalton macrophage membrane protein homologous to the mammalian lectin galectin-3." Infect Immun (2000), 68:4391-4398.
Geijtenbeek, T. B., et al., "DC-SIGN-ICAM-2 interaction mediates dendritic cell trafficking." Nat Immunol (2000), 1:353-357.
Geijtenbeek, T. B., et al., "Identification of DC-SIGN, a novel dendritic cell-specific ICAM-3 receptor that supports primary immune responses." Cell (2000), 100:575-585.
Geijtenbeek, T. B., et al., "Mycobacteria target DC-SIGN to suppress dendritic cell function." J Exp Med (2003), 197:7-17.
Gross, J. A., et al., "TACI and BCMA are receptors for a TNF homologue implicated in B-cell autoimmune disease." Nature (2000), 404:995-999.
Jeannin, P., B. et al., "Complexity and complementarity of outer membrane protein A recognition by cellular and humoral innate immunity receptors." Immunity (2005), 22:551-560.
Kikuchi, T., S. Worgall, R. Singh, M. A. Moore, and R. G. Crystal. 2000. Dendritic cells genetically modified to express CD40 ligand and pulsed with antigen can initiate antigen-specific humoral immunity independent of CD4+ T cells. Nat Med (2000), 6:1154-1159.
Lee, S. J., et al., "Mannose receptor-mediated regulation of serum glycoprotein homeostasis." Science (2002), 295:1898-1901.
Maclennan, I., et al., "Dendritic cells, BAFF, and APRIL: innate players in adaptive antibody responses." Immunity (2002), 17:235-238.

(Continued)

*Primary Examiner* — Amy Juedes
(74) *Attorney, Agent, or Firm* — Fulbright & Jaworski LLP

(57) ABSTRACT

The present invention includes compositions and methods for targeting the LOX-1 receptor on immune cells and uses for the anti-LOX-1 antibodies.

8 Claims, 10 Drawing Sheets

OTHER PUBLICATIONS

Maeda, N., et al., "The cell surface receptor DC-SIGN discriminates between Mycobacterium species through selective recognition of the mannose caps on lipoarabinomannan." J Biol Chem (2003), 278:5513-5516.

Moore, P. A., et al., "BLyS: member of the tumor necrosis factor family and B lymphocyte stimulator." Science (1999), 285:260-263.

Netea, M. G., et al., "CD40/CD40 ligand interactions in the host defense against disseminated *Candida albicans* infection: the role of macrophage-derived nitric oxide." Eur J Immunol (2002), 32:1455-1463.

Pyz, E., et al., "C-type lectin-like receptors on myeloid cells." Ann Med (2006), 38:242-251.

Qi, H., et al., "Extrafollicular activation of lymph node B cells by antigen-bearing dendritic cells." Science (2006), 312:1672-1676.

Ruprecht, C. R., et al., "Toll-like receptor stimulation as a third signal required for activation of human naive B cells." Eur J Immunol (2006), 36:810-816.

Tailleux, L., et al., "DC-SIGN is the major Mycobacterium tuberculosis receptor on human dendritic cells." J Exp Med (2003), 197:121-127.

Wykes, M., et al., "Dendritic cell-B-cell interaction: dendritic cells provide B cells with CD40-independent proliferation signals and CD40-dependent survival signals." Immunology (2000), 100:1-3.

International Search Report and Written Opinion for PCT/US2008/054792 dated Aug. 13, 2008.

International Search Report and Written Opinion for PCT/US 2008/054785 dated Sep. 25, 2008.

International Search Report and Written Opinion for PCT/US2008/054798 dated Dec. 8, 2008.

Ramakrishna, et al., "Toll-like receptor activation enhances cell-mediated immunity induced by an antibody vaccine targeting human dendritic cells," Journal of Translational Medicine (2007), 5:5.

Schaft, et al. "Dendritic cell vaccination and other strategies to tip the balance of the immune system." Cancer Immunol immunother 2008, 57:913-928.

* cited by examiner

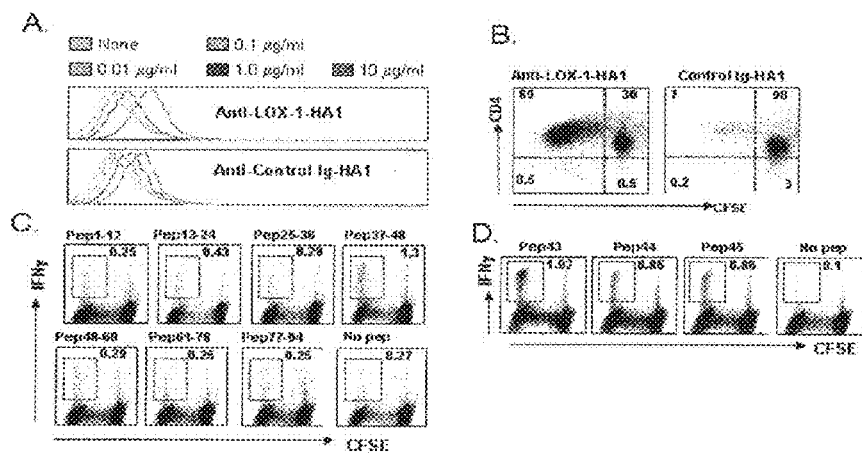

ACTIVATION OF HUMAN ANTIGEN-PRESENTING CELLS THROUGH DENDRITIC CELL LECTIN-LIKE OXIDIZED LDL RECEPTOR-1 (LOX-1)

CROSS-REFERENCE TO RELATED APPLICATIONS

This application claims priority to U.S. Provisional Application Ser. No. 60/891,424, filed Feb. 23, 2007 and is related to U.S. Provisional application Ser. No. 12/036,095, filed Feb. 22, 2008, and Ser. No. 12/036,158, filed Feb. 22, 2008, the entire contents of which are incorporated herein by reference.

STATEMENT OF FEDERALLY FUNDED RESEARCH

This invention was made with U.S. Government support under Contract No. 1U19AI057234-0100003 awarded by the NIH. The government has certain rights in this invention.

TECHNICAL FIELD OF THE INVENTION

The present invention relates in general to the field of immune cell activation, and more particularly, to compositions and methods for activating immune cells through the LOX-1 receptor.

BACKGROUND OF THE INVENTION

Without limiting the scope of the invention, its background is described in connection with dendritic cell activation.

Dendritic Cells play a pivotal role in controlling the interface of innate and acquired immunity by providing soluble and intercellular signals, followed by recognition of pathogens. These functions of DCs are largely dependent on the expression of specialized surface receptors, 'pattern recognition receptors' (PRRs), represented, most notably, by toll-like receptors (TLRs) and C-type lectins or lectin-like receptors (LLRs) (2-4).

In the current paradigm, a major role of TLRs is to alert DCs to produce interleukin 12 (IL-12) and other inflammatory cytokines for initiating immune responses. C-type LLRs operate as constituents of the powerful antigen capture and uptake mechanism of macrophages and DCs (2). Compared to TLRs, however, LLRs might have broader ranges of biological functions that include cell migration (5) and intercellular interactions (6). These multiple functions of LLRs might be due to the fact that LLRs, unlike TLRs, can recognize both self and non-self. However, the complexity of LLRs, including the redundancy of a number of LLRs expressed in immune cells, has been one of the major obstacles to understand the detailed functions of individual LLRs. In addition, natural ligands for most of these receptors remain unidentified. Nonetheless, evidence from recent studies suggests that LLRs, in collaboration with TLRs, may contribute to the activation of immune cells during microbial infections (7-15).

SUMMARY OF THE INVENTION

The present invention includes novel compositions and methods for targeting and using anti-human LOX-1 monoclonal antibodies (mAbs) and characterized their biological functions. The anti-LOX-1 mAbs and fragments thereof are shown to be useful for the targeting, characterization and activation of immune cells. The present inventors recognized that, while LOX-1 is capable of directing the internalization of surrogate antigen into human DC, the present invention identifies and uses novel biological activities of LOX-1 to effect particularly desirable changes in the immune system, some in the context of antigen uptake (e.g., vaccination), others through the unique action of LOX-1 effectors (alone or in concert with other immune regulatory molecules) capable of eliciting signaling through this receptor on DC, B cells, and monocytes. The invention disclosure reveals means of developing unique agents capable of activating cells bearing LOX-1, as well as the effect of the resulting changes in cells receiving these signals regards action on other cells in the immune system. These effects [either alone, or in concert with other signals (i.e., co-stimulation)] are highly predictive of therapeutic outcomes for certain disease states or for augmenting protective outcomes in the context of vaccination.

LOX-1 was originally identified as a receptor of oxidized low-density lipoprotein (OxLDL) on endothelial cells and has been extensively investigated in association with atherosclerosis. OxLDL-mediated endothelial activation, dysfunction and injury play a key role in the progression of atherosclerosis in its very early phase. LOX-1 reportedly mediates OxLDL signals, inducing reactive oxygen species production, an upregulated expression of endothelin-1, MCP-1 and adhesion molecules mediated by NF-kB activation, and apoptosis. Although LOX-1 is classified as a type D scavenger receptor, endocytosis of OxLDL by macrophages, leading to foam cell formation, has been shown to be mediated mainly by other scavenger receptors. LOX-1 reportedly can internalize apoptotic/aged cells. LOX-1 can also recognize bacterial components. LOX-1 expression has been observed in immature myeloid DCs as well as monocyte-derived DCs, monocytes, macrophages and B cells.

DCs can cross-present protein antigens (Rock K L *Immunol Rev.* 2005 October; 207:166-83). In vivo, DCs take up antigens by the means of a number of receptors and present antigenic peptides in both class I and II. In particular, LOX-1 is a 'pattern recognition' receptor that efficiently uptakes antigens and cross-presents antigenic peptides (Delneste Y Immunity 2002 17: 353). In the mouse model, indeed, antigen conjugated with anti-LOX-1 was sufficient to induce immune responses to the tumor challenged. However, activation by a bacterial component could not be observed through LOX-1 (1) alone and co-localizing TLR2 was shown to be responsible for the activation signaling. In LOX-1, neither a cytoplasmic tyrosine residue nor a transmembrane cationic amino acid is known to have signaling function.

The present invention includes compositions and methods for increasing the effectiveness of antigen presentation by a LOX-1-expressing antigen presenting cell by isolating a LOX-1-specific antibody or fragment thereof capable of activating the antigen presenting cell and contacting the antigen presenting cell with an anti-LOX-1-specific antibody or fragment thereof, wherein the antigen presenting cell is activated. The antigen presenting cell may be an isolated dendritic cell, a peripheral blood mononuclear cell, a monocyte, a myeloid dendritic cell and combinations thereof. The antigen presenting cell may be an isolated dendritic cell, a peripheral blood mononuclear cell, a monocyte, a B cell, a myeloid dendritic cell and combinations thereof that has been cultured in vitro with GM-CSF and IL-4, interferon alpha, antigen and combinations thereof. The method may also include the step of activating the antigen presenting cells contacted with GM-CSF and IL-4 or Interferon alpha, wherein contact with the LOX-1-specific antibody or fragment thereof increases the surface expression of CD86 and HLA-DR on the antigen presenting cell. For example, the antigen presenting cells may be a dendritic cell that has been contacted with the LOX-1-specific antibody or fragment thereof, GM-CSF and IL-4 or Interferon alpha to activate the dendritic cell, wherein the activated dendritic cells increases the surface expression of CD86, CD80, and HLA-DR. In another example, the antigen presenting cell may be a dendritic cell that has been contacted with the LOX-1-specific antibody or fragment thereof, GM-CSF and IL-4 or Interferon alpha to activate the dendritic cell, wherein the activated dendritic cells increases the secretion of IL-12p40, MCP-1, IL-8, TNFa, IL-6, MIP-1a, and IL-1b and combinations thereof, and/or may increase its activation in conjunction with signaling through CD40. It has also been found that the antigen presenting cells include a dendritic cell that has been contacted with GM-CSF and IL-4 or Interferon alpha and the LOX-1-specific antibody or fragment thereof has increased co-stimulatory activity of dendritic cells. Specific examples of genes that have a change in expression profile upon exposure to the LOX-1-specific antibody or fragment thereof of the present invention include those one or more genes as shown in FIG. 4. Non-limiting examples of the LOX-1-specific antibody or fragment thereof may be selected from clone 9D7-10-4, 8B4-10-2, 11C8-B7, 13B11-A8 and combinations thereof. The dendritic cells that are activated through the LOX-1 with the LOX-1-specific antibody or fragment thereof are capable of activating B cells, T cells and combinations thereof.

The present invention also includes a recombinant antibody (rAb) in which LOX-1-specific antibody or fragment thereof is bound to one half of a Cohesin/Dockerin pair. The LOX-1-specific antibody or fragment thereof that is part of the rAb may be bound to one half of a Cohesin/Dockerin pair and the other half of the pair may be bound to one or more cytokines selected from interleukins, transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives of such growth factors, B/T-cell differentiation factors, B/T-cell growth factors, mitogenic cytokines, chemotactic cytokines and chemokines, colony stimulating factors, angiogenesis factors, IFN-α, IFN-β, IFN-γ, IL1, IL2, IL3, IL4, IL5, IL6, IL7, IL8, IL9, IL10, IL11, IL12, IL13, IL14, IL15, IL16, IL17, IL18, etc., leptin, myostatin, macrophage stimulating protein, platelet-derived growth factor, TNF-α, TNF-β, NGF, CD40L, CD137L/4-1BBL, human lymphotoxin-β, G-CSF, M-CSF, GM-CSF, PDGF, IL-1α, IL1-β, IP-10, PF4, GRO, 9E3, erythropoietin, endostatin, angiostatin, VEGF, transforming growth factor (TGF) supergene family include the beta transforming growth factors (for example TGF-β1, TGF-β2, TGF-β3); bone morphogenetic proteins (for example, BMP-1, BMP-2, BMP-3, BMP-4, BMP-5, BMP-6, BMP-7, BMP-8, BMP-9); heparin-binding growth factors (fibroblast growth factor (FGF), epidermal growth factor (EGF), platelet-derived growth factor (PDGF), insulin-like growth factor (IGF)); Inhibins (for example, Inhibin A, Inhibin B); growth differentiating factors (for example, GDF-1); and Activins (for example, Activin A, Activin B, Activin AB).

The present invention also includes a hybridoma that expressed a LOX-1-specific antibody or fragment thereof, wherein the LOX-1-specific antibody or fragment thereof activates an antigen presenting cell to express new surface markers, secrete one or more cytokines or both. Non-limiting examples of the hybridoma include clone 9D7-10-4, 8B4-10-2, 11C8-B7, 13B11-A8 and combinations thereof.

The present invention also includes a method for enhancing B cell immune responses by triggering a LOX-1 receptor on a dendritic cell with a LOX-1 specific antibody or fragment thereof in the presence of antigen, wherein a B cell that is contacted with the LOX-1 activated dendritic cell increases antibody production, secretes cytokines, increase B cell activation surface marker expression and combinations thereof. The B cells activated using the present invention may secrete IL-8, MIP-1a, IL-6, TNFa and combinations thereof, may be a plasma cells, activate B cells to express LOX-1, and/or trigger the B cell to increase production of IgG, IgM, IgA and combinations thereof.

In another method, the present invention includes enhancing B cell immune responses by triggering a LOX-1 receptor on a B-cell with a LOX-1 specific antibody or fragment thereof, wherein the B cell increases antibody production, secreted IL-8, MIP-1α, IL-6, TNFa and combinations thereof, and/or increase production of IgG, IgM, IgA and combinations thereof.

The present invention also includes a method for enhancing T cell activation by triggering a LOX-1 receptor on a dendritic cell with a LOX-1 specific antibody or fragment and contacting a T cell to the LOX-1 activated dendritic cell, wherein T cell activation is enhanced. The dendritic cells may be contacted with GM-CSF and IL-4, interferon alpha, antigen and combinations thereof and cause the activation of CD8+ T cells. In one embodiment, the T cells proliferate upon exposure to dendritic cells activated with anti-LOX-1 antibodies or fragments thereof.

The present invention also includes an anti-LOX-1 immunoglobulin or portion thereof that is secreted from mammalian cells and an antigen bound to the immunoglobulin, wherein the immunoglobulin targets the antigen to antigen presenting cells. The immunoglobulin may include one or more antigen specific domain selected from a full length antibody, an antibody variable region domain, an Fab fragment, a Fab' fragment, an F(ab)2 fragment, and Fv fragment, and Fabc fragment and/or a Fab fragment with portions of the Fc domain. The antibody or fragments thereof may be used to produce a vaccine that includes a dendritic cell activated with a LOX-1-specific antibody or fragment thereof.

The present invention also includes the use of agents that engage the LOX-1 receptor on immune cells, alone or with co-activating agents, the combination activating antigen-presenting cells for therapeutic applications; use of a LOX-1 binding agent linked to one or more antigens, with or without activating agents, on immune cells to make a vaccine; use of anti-LOX-1 agents as co-activating agents of immune cells for the enhancement of immune responses directed through a cell surface receptor other than LOX-1 expressed on immune cells; use of anti-LOX-1 antibody V-region sequences capable of binding to and activating immune cells through the LOX-1 receptor and/or use of DC-LOX-1 binding agents linked to one or more toxic agents for therapeutic purposes in the context of diseases known or suspected to result from inappropriate activation of immune cells via LOX-1 or in the context of pathogenic cells or tissues that express LOX-1.

The present invention also includes a modular rAb carrier that includes a LOX-1-specific antibody binding domain linked to one or more antigen carrier domains that comprise one half of a cohesin-dockerin binding pair. The antigen-specific binding domain of the rAb will include at least a portion of an antibody, for example, antigen-specific binding domain may include at least a portion of an antibody in a fusion protein with the one half of the cohesin-dockerin binding pair. The rAb may include a complementary half of the cohesin-dockerin binding pair bound to an antigen that forms a complex with the modular rAb carrier or a complementary half of the cohesin-dockerin binding pair that is a fusion protein with an antigen. The antigen specific domain may be a full length antibody, an antibody variable region domain, an Fab fragment, a Fab' fragment, an F(ab)2 fragment, and Fv fragment, and Fabc fragment and/or a Fab fragment with portions of the Fc domain.

BRIEF DESCRIPTION OF THE DRAWINGS

For a more complete understanding of the features and advantages of the present invention, reference is now made to the detailed description of the invention along with the accompanying figures and in which:

FIG. 1A. PBMCs from normal donors were stained with anti-CD 11c, CD14, CD19, and CD3 with anti-LOX-1 mAb. Cells stained with individual antibodies were gated to measure the expression levels of LOX-1. FIG. 1B. Monocytes from normal donors were cultured in the presence of GM-CSF with IL-4 (IL-4DCs) or IFNa (IFNDCs), and cells were stained with anti-LOX-1 mAb. C. Myeloid DCs (Lin-HLA-DR+CD11c+CD123−) were purified from blood by a FACS sorter, and stained with anti-LOX-1 mAb.

FIG. 1C shows the binding rank order 15C4>10F9>1G6>>commercial anti-LOX-1 in capturing LOX-1 ectodomain in solution. 15C4-10-1 and 15C4.1 are two independent preparations of antibody from two subclones of the initial 15C4 hybridoma.

FIG. 2A. Cells were stained with anti-CD86. FIG. 2B. Culture supernatants were analyzed to measure cytokines and chemokines by Luminex.

FIG. 3A. IL-4DCs were stimulated with anti-LOX-1 for 24 h, and then cells were stained with anti-CD86 and HLA-DR. FIG. 3B. Myeloid DCs were purified from blood by FACS sorting, and cells were stained with anti-CD86, CD80, and HLA-DR.

FIG. 7A shows day six staining of cells stained with fluorescently labeled antibodies. CD3$^+$ and 7-AAD$^+$ cells were gated out. CD38$^+$ and CFSE$^-$ cells were purified by a FACS sorter and Giemsa staining was performed. FIG. 7B shows culture supernatants on day thirteen analyzed for total IgM by sandwich ELISA. FIG. 7C shows DCs that were pulsed with 5 moi of heat-inactivated influenza virus (PR8), and cultured with B cells. Culture supernatant was analyzed for influenza-specific immunoglobulins (Igs) on day thirteen. FIG. 7D shows the results of CFSE-labeled $5\times10^5$ PBMCs from buffy coats that were cultured in mAb-coated plates with (lower panels) or without (upper panels) 50 nM CpG. Cells were stained with anti-CD38 on day seven. CD3$^+$ and 7-AAD$^+$ cells were gated out. FIG. 7E shows culture supernatants from the PBMCs culture were analyzed for measuring total Igs by ELISA on day thirteen. Data from six day GM/IL-4 DCs cultured in mAb-coated plates for 48 h, and expression levels of APRIL were determined by intracellular staining of the cells. Dotted lines are cells stained with control antibody (data not shown). Thin and thick lines represent cells incubated in the plates coated with anti-LOX-1 or control mAbs, respectively. Data are representative of two separate experiments using cells from three different normal donors each time.

FIG. 8A shows PBMCs from buffy coats were stained with anti-CD19, anti-CD3, and anti-LOX-1 or control mAbs. CD19$^+$ cells were gated and the expression levels of the molecules on CD19$^+$ B cells were measured by flow cytometry. FIG. 8B shows CD 19$^+$ B cells that were cultured in plates coated with the mAbs for 16-18 h, and then culture supernatants were analyzed for cytokines and chemokines by Luminex. FIG. 8C shows $1\times10^5$ CD19$^+$ B cells were cultured in plates coated with the mAbs for thirteen days. Total Ig levels were measured by ELISA. Data are representative of two repeat experiments using cells from three different normal donors.

FIG. 9A shows 5×103 of six day GM/IL-4 DCs were cultured in plates coated with anti-LOX-1 or control mAbs for 16-18 h, and then purified allogeneic T cells were co-cultured. Cells were pulsed with 3-[H]-thymidine, 1 uCi/well, for 18 h before harvesting. 3-[H]-thymidine uptake was measured by b-counter. FIGS. 9B and 9C show six day GM/IL-4 DCs (5×103/well) were incubated in plates coated with the mAbs in the presence of 20 uM Mart-1 peptide (A) or 27 ug/ml recombinant fusion protein of Mart-1 (B) for 16 h. 2×106 purified autologous CD8 T cells were co-cultured for ten days. On day two, 20 units/ml IL-2 and 10 units/ml of IL-7 were added to the culture. Cells were stained with anti-CD8 and Mart-1-tetramer. FIG. 9C shows 5×105 PBMCs from buffy coats that were cultured with 0.1 uM Flu M1 peptide in plates coated with the mAbs for one week. Cells were stained with anti-CD8 and Flu M1 tetramer. D. IL-4DCs were loaded with 10 or 1 nM of anti-LOX-1-Flu M1 or control Ig-Flu M1 fusion protein for 2 h. 2×106 purified autologous CD8 T cells were co-cultured for 7 days. Cells were stained with anti-CD8 and Flu M1 specific tetramer.

Figure 10:
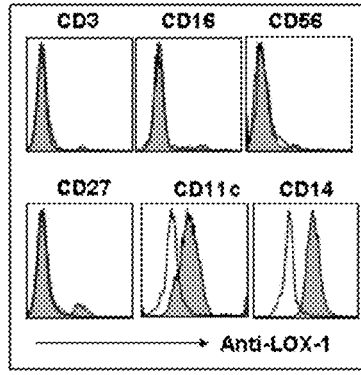

FIG. 10 shows that PBMC from non-human primates (Cynomolgus) were stained with anti-LOX-1 mAb and antibodies to cell surface markers.

Figure 11:
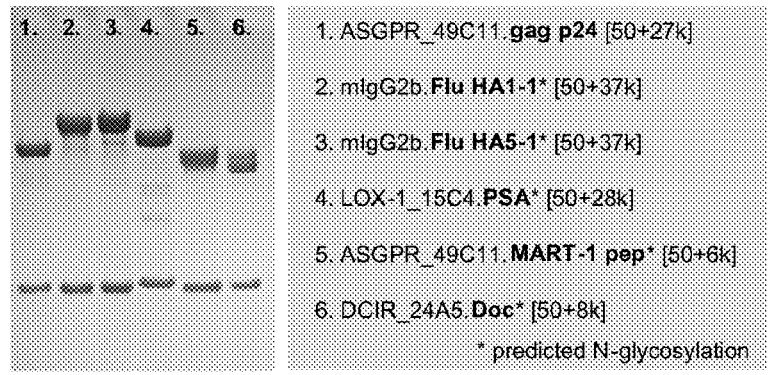

FIG. 11 shows reduced SDS.PAGE analysis of typical rAb.antigen fusion proteins—including anti-LOX-1.15C4.PSA, which is capable of directing prostate-specific antigen (highlighted grey) to the surface of antigen-presenting cells for the purpose of vaccination against prostate cancer.

Figure 12:
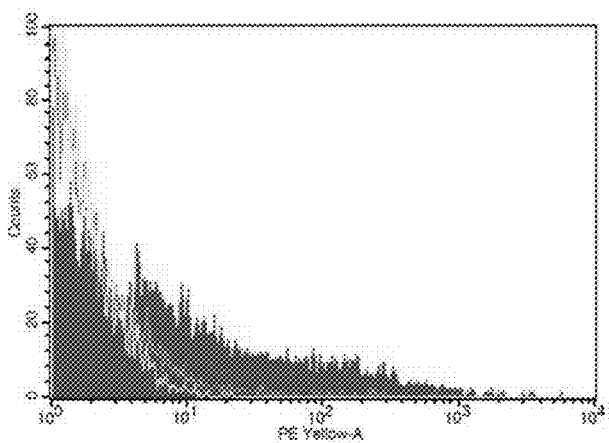

FIG. 12 shows anti-LOX-1.Doc:Coh.Flu M1 complexes deliver Flu M1 to the surface of CHO cells transfected with LOX-1 cDNA. 1 ug/ml (filled red plot) of anti-LOX-1.Doc rAb or control hIgG4.Doc rAb (green plot) were incubated with biotinylated Coh.Flu M1 (2 ug/ml) for 1 hr at R.T. transfected CHO cells were added and incubation continued for 20 min on ice. Cells were then washed and stained with PE-labeled streptavidin. Cells were then analyzed for PE fluorescence (X axis is intensity). Plot for anti-LOX-1.Doc complex versus untransfected CHO cells is shown in yellow.

FIG. 13 shows anti-LOX-1 mAb staining of a section of human tonsil. The red stained cells are specific populations of LOX-1-bearing cells in the area surrounding the germinal centers. This and other tissue staining with anti-LOX-1 mAbs reveal that very specific tissue cells in the human body express LOX-1. Such methods can be used to show that the mAbs developed for e.g., antigen targeting are specific and that cells bearing LOX-1 are present in the body—ready targets for therapeutic anti-LOX-1 agents.

FIGS. 14A and 14B show the mucosal-homing of B cells by DCs activated with anti-LOX-1 mAb.

FIG. 15 shows that anti-LOX-1 mAb contribute to the enhanced production of IgA1 and IgA2.

FIG. 18 shows that an anti-LOX-1 vaccine can elicit DC-subset-specific immune responses.

FIG. 19 shows the cross-reactivity of anti-LOX-1 antibodies to macaque LOX-1.

FIG. 20 shows a Clustal W alignment of the four variants of sequences from macaques (5U1-5U4) with human LOX-1.

FIG. 21A to 21D show that antigens delivered through LOX-1 result in antigen specific CD4 T cell responses

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "modular rAb carrier" is used to describe a recombinant antibody system that has been engineered to provide the controlled modular addition of diverse antigens, activating proteins, or other antibodies to a single recombinant monoclonal antibody (mAb), in this case, an anti-LOX-1 monoclonal antibody. The rAb may be a monoclonal antibody made using standard hybridoma techniques, recombinant antibody display, humanized monoclonal antibodies and the like. The modular rAb carrier can be used to, e.g., target (via one primary recombinant antibody against an internalizing receptor, e.g., a human dendritic cell receptor) multiple antigens and/or antigens and an activating cytokine to dendritic cells (DC). The modular rAb carrier may also be used to join two different recombinant mAbs end-to-end in a controlled and defined manner.

The antigen binding portion of the "modular rAb carrier" may be one or more variable domains, one or more variable and the first constant domain, an Fab fragment, a Fab' fragment, an $F(ab)_2$ fragment, and Fv fragment, and Fabc fragment and/or a Fab fragment with portions of the Fc domain to which the cognate modular binding portions are added to the amino acid sequence and/or bound. The antibody for use in the modular rAb carrier can be of any isotype or class, subclass or from any source (animal and/or recombinant).

In one non-limiting example, the modular rAb carrier is engineered to have one or more modular cohesin-dockerin protein domains for making specific and defined protein complexes in the context of engineered recombinant mAbs. The mAb is a portion of a fusion protein that includes one or more modular cohesin-dockerin protein domains carboxy from the antigen binding domains of the mAb. The cohesin-dockerin protein domains may even be attached post-translationally, e.g., by using chemical cross-linkers and/or disulfide bonding.

The term "antigen" as used herein refers to a molecule that can initiate a humoral and/or cellular immune response in a recipient of the antigen. Antigen may be used in two different contexts with the present invention: as a target for the antibody or other antigen recognition domain of the rAb or as the molecule that is carried to and/or into a cell or target by the rAb as part of a dockerin/cohesin-molecule complement to the modular rAb carrier. The antigen is usually an agent that causes a disease for which a vaccination would be advantageous treatment. When the antigen is presented on MHC, the peptide is often about 8 to about 25 amino acids. Antigens include any type of biologic molecule, including, for example, simple intermediary metabolites, sugars, lipids and hormones as well as macromolecules such as complex carbohydrates, phospholipids, nucleic acids and proteins. Common categories of antigens include, but are not limited to, viral antigens, bacterial antigens, fungal antigens, protozoal and other parasitic antigens, tumor antigens, antigens involved in autoimmune disease, allergy and graft rejection, and other miscellaneous antigens.

The modular rAb carrier is able to carry any number of active agents, e.g., antibiotics, anti-infective agents, antiviral agents, anti-tumoral agents, antipyretics, analgesics, anti-inflammatory agents, therapeutic agents for osteoporosis, enzymes, cytokines, anticoagulants, polysaccharides, collagen, cells, and combinations of two or more of the foregoing active agents. Examples of antibiotics for delivery using the present invention include, without limitation, tetracycline, aminoglycosides, penicillins, cephalosporins, sulfonamide drugs, chloramphenicol sodium succinate, erythromycin, vancomycin, lincomycin, clindamycin, nystatin, amphotericin B, amantidine, idoxuridine, p-amino salicyclic acid, isoniazid, rifampin, antinomycin D, mithramycin, daunomycin, adriamycin, bleomycin, vinblastine, vincristine, procarbazine, imidazole carboxamide, and the like.

Examples of anti-tumor agents for delivery using the present invention include, without limitation, doxorubicin, Daunorubicin, taxol, methotrexate, and the like. Examples of antipyretics and analgesics include aspirin, Motrin®, Ibuprofen®, naprosyn, acetaminophen, and the like.

Examples of anti-inflammatory agents for delivery using the present invention include, without limitation, include NSAIDS, aspirin, steroids, dexamethasone, hydrocortisone, prednisolone, Diclofenac Na, and the like.

Examples of therapeutic agents for treating osteoporosis and other factors acting on bone and skeleton include for delivery using the present invention include, without limitation, calcium, alendronate, bone GLa peptide, parathyroid hormone and its active fragments, histone H4-related bone formation and proliferation peptide and mutations, derivatives and analogs thereof.

Examples of enzymes and enzyme cofactors for delivery using the present invention include, without limitation, pancrease, L-asparaginase, hyaluronidase, chymotrypsin, trypsin, tPA, streptokinase, urokinase, pancreatin, collagenase, trypsinogen, chymotrypsinogen, plasminogen, streptokinase, adenyl cyclase, superoxide dismutase (SOD), and the like.

Examples of cytokines for delivery using the present invention include, without limitation, interleukins, transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives of such growth factors. Cytokines may be B/T-cell differentiation factors, B/T-cell growth factors, mitogenic cytokines, chemotactic cytokines, colony stimulating factors, angiogenesis factors, IFN-$\alpha$, IFN-$\beta$, IFN-$\gamma$, IL1, IL2, IL3, IL4, IL5, IL6, IL7, IL8, IL9, IL10, IL11, IL12, IL13, IL14, IL15, IL16, IL17, IL18, etc., leptin, myostatin, macrophage stimulating protein, platelet-derived growth factor, TNF-$\alpha$, TNF-$\beta$, NGF, CD40L, CD137L/4-1BBL, human lymphotoxin-$\beta$, G-CSF, M-CSF, GM-CSF, PDGF, IL-1$\alpha$, IL1-$\beta$, IP-10, PF4, GRO, 9E3, erythropoietin, endostatin, angiostatin, VEGF or any fragments or combinations thereof. Other cytokines include members of the transforming growth factor (TGF) supergene family include the beta transforming growth factors (for example TGF-$\beta$1, TGF-$\beta$2, TGF-$\beta$3); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)); Inhibins (for example, Inhibin A, Inhibin B); growth differentiating factors (for example, GDF-1); and Activins (for example, Activin A, Activin B, Activin AB).

Examples of growth factors for delivery using the present invention include, without limitation, growth factors that can be isolated from native or natural sources, such as from mammalian cells, or can be prepared synthetically, such as by recombinant DNA techniques or by various chemical processes. In addition, analogs, fragments, or derivatives of these factors can be used, provided that they exhibit at least some of the biological activity of the native molecule. For example, analogs can be prepared by expression of genes altered by site-specific mutagenesis or other genetic engineering techniques.

Examples of anticoagulants for delivery using the present invention include, without limitation, include warfarin, heparin, Hirudin, and the like. Examples of factors acting on the immune system include for delivery using the present invention include, without limitation, factors which control inflammation and malignant neoplasms and factors which attack infective microorganisms, such as chemotactic peptides and bradykinins.

Examples of viral antigens include, but are not limited to, e.g., retroviral antigens such as retroviral antigens from the human immunodeficiency virus (HIV) antigens such as gene products of the gag, pol, and env genes, the Nef protein, reverse transcriptase, and other HIV components; hepatitis viral antigens such as the S, M, and L proteins of hepatitis B virus, the pre-S antigen of hepatitis B virus, and other hepatitis, e.g., hepatitis A, B, and C, viral components such as hepatitis C viral RNA; influenza viral antigens such as hemagglutinin and neuraminidase and other influenza viral components; measles viral antigens such as the measles virus fusion protein and other measles virus components; rubella viral antigens such as proteins E1 and E2 and other rubella virus components; rotaviral antigens such as VP7sc and other rotaviral components; cytomegaloviral antigens such as envelope glycoprotein B and other cytomegaloviral antigen components; respiratory syncytial viral antigens such as the RSV fusion protein, the M2 protein and other respiratory syncytial viral antigen components; herpes simplex viral antigens such as immediate early proteins, glycoprotein D, and other herpes simplex viral antigen components; varicella zoster viral antigens such as gpI, gpII, and other varicella zoster viral antigen components; Japanese encephalitis viral antigens such as proteins E, M-E, M-E-NS1, NS1, NS1-NS2A, 80% E, and other Japanese encephalitis viral antigen components; rabies viral antigens such as rabies glycoprotein, rabies nucleoprotein and other rabies viral antigen components. See Fundamental Virology, Second Edition, eds. Fields, B. N. and Knipe, D. M. (Raven Press, New York, 1991) for additional examples of viral antigens.

Antigenic targets that may be delivered using the rAb-DC/DC-antigen vaccines of the present invention include genes encoding antigens such as viral antigens, bacterial antigens, fungal antigens or parasitic antigens. Viruses include picornavirus, coronavirus, togavirus, flavirvirus, rhabdovirus, paramyxovirus, orthomyxovirus, bunyavirus, arenavirus, reovirus, retrovirus, papilomavirus, parvovirus, herpesvirus, poxvirus, hepadnavirus, and spongiform virus. Other viral targets include influenza, herpes simplex virus 1 and 2, measles, dengue, smallpox, polio or HIV. Pathogens include trypanosomes, tapeworms, roundworms, helminthes, malaria. Tumor markers, such as fetal antigen or prostate specific antigen, may be targeted in this manner. Other examples include: HIV env proteins and hepatitis B surface antigen. Administration of a vector according to the present invention for vaccination purposes would require that the vector-associated antigens be sufficiently non-immunogenic to enable long term expression of the transgene, for which a strong immune response would be desired. In some cases, vaccination of an individual may only be required infrequently, such as yearly or biennially, and provide long term immunologic protection against the infectious agent. Specific examples of organisms, allergens and nucleic and amino sequences for use in vectors and ultimately as antigens with the present invention may be found in U.S. Pat. No. 6,541,011, relevant portions incorporated herein by reference, in particular, the tables that match organisms and specific sequences that may be used with the present invention.

Bacterial antigens for use with the rAb vaccine disclosed herein include, but are not limited to, e.g., bacterial antigens such as pertussis toxin, filamentous hemagglutinin, pertactin, FIM2, FIM3, adenylate cyclase and other pertussis bacterial antigen components; diptheria bacterial antigens such as diptheria toxin or toxoid and other diptheria bacterial antigen components; tetanus bacterial antigens such as tetanus toxin or toxoid and other tetanus bacterial antigen components; streptococcal bacterial antigens such as M proteins and other streptococcal bacterial antigen components; gram-negative bacilli bacterial antigens such as lipopolysaccharides and other gram-negative bacterial antigen components, *Mycobacterium tuberculosis* bacterial antigens such as mycolic acid, heat shock protein 65 (HSP65), the 30 kDa major secreted protein, antigen 85A and other mycobacterial antigen components; *Helicobacter pylori* bacterial antigen components; pneumococcal bacterial antigens such as pneumolysin, pneumococcal capsular polysaccharides and other pneumococcal bacterial antigen components; *haemophilus influenza* bacterial antigens such as capsular polysaccharides and other *haemophilus influenza* bacterial antigen components; anthrax bacterial antigens such as anthrax protective antigen and other anthrax bacterial antigen components; rickettsiae bacterial antigens such as rompA and other rickettsiae bacterial antigen component. Also included with the bacterial antigens described herein are any other bacterial, mycobacterial, mycoplasmal, rickettsial, or chlamydial antigens. Partial or whole pathogens may also be: *haemophilus influenza; Plasmodium falciparum; neisseria meningitidis; streptococcus pneumoniae; neisseria gonorrhoeae; salmonella* serotype typhi; *shigella; vibrio cholerae*; Dengue Fever; Encephalitides; Japanese Encephalitis; lyme disease; *Yersinia pestis*; west nile virus; yellow fever; tularemia; hepatitis (viral; bacterial); RSV (respiratory syncytial virus); HPIV 1 and HPIV 3; adenovirus; small pox; allergies and cancers.

Fungal antigens for use with compositions and methods of the invention include, but are not limited to, e.g., candida fungal antigen components; *histoplasma* fungal antigens such as heat shock protein 60 (HSP60) and other *histoplasma* fungal antigen components; cryptococcal fungal antigens such as capsular polysaccharides and other cryptococcal fungal antigen components; *coccidiodes* fungal antigens such as spherule antigens and other *coccidiodes* fungal antigen components; and tinea fungal antigens such as trichophytin and other *coccidiodes* fungal antigen components.

Examples of protozoal and other parasitic antigens include, but are not limited to, e.g., *plasmodium falciparum* antigens such as merozoite surface antigens, sporozoite surface antigens, circumsporozoite antigens, gametocyte/gamete surface antigens, blood-stage antigen pf 155/RESA and other plasmodial antigen components; *toxoplasma* antigens such as SAG-1, p30 and other toxoplasmal antigen components; schistosomae antigens such as glutathione-S-transferase, paramyosin, and other schistosomal antigen components; *leishmania major* and other leishmaniae antigens such as gp63, lipophosphoglycan and its associated protein and other leishmanial antigen components; and *trypanosoma cruzi* antigens such as the 75-77 kDa antigen, the 56 kDa antigen and other trypanosomal antigen components.

Antigen that can be targeted using the rAb of the present invention will generally be selected based on a number of factors, including: likelihood of internalization, level of immune cell specificity, type of immune cell targeted, level of immune cell maturity and/or activation and the like. Examples of cell surface markers for dendritic cells include, but are not limited to, MHC class I, MHC Class II, B7-2, CD18, CD29, CD31, CD43, CD44, CD45, CD54, CD58, CD83, CD86, CMRF-44, CMRF-56, DCIR and/or DEC-TIN-1 and the like; while in some cases also having the absence of CD2, CD3, CD4, CD8, CD14, CD15, CD16, CD 19, CD20, CD56, and/or CD57. Examples of cell surface markers for antigen presenting cells include, but are not limited to, MHC class I, MHC Class II, CD40, CD45, B7-1, B7-2, IFN-γ receptor and IL-2 receptor, ICAM-1 and/or Fcγ receptor. Examples of cell surface markers for T cells include, but are not limited to, CD3, CD4, CD8, CD 14, CD20, CD11b, CD16, CD45 and HLA-DR.

Target antigens on cell surfaces for delivery includes those characteristic of tumor antigens typically will be derived from the cell surface, cytoplasm, nucleus, organelles and the like of cells of tumor tissue. Examples of tumor targets for the antibody portion of the present invention include, without limitation, hematological cancers such as leukemias and lymphomas, neurological tumors such as astrocytomas or glioblastomas, melanoma, breast cancer, lung cancer, head and neck cancer, gastrointestinal tumors such as gastric or colon cancer, liver cancer, pancreatic cancer, genitourinary tumors such cervix, uterus, ovarian cancer, vaginal cancer, testicular cancer, prostate cancer or penile cancer, bone tumors, vascular tumors, or cancers of the lip, nasopharynx, pharynx and oral cavity, esophagus, rectum, gall bladder, biliary tree, larynx, lung and bronchus, bladder, kidney, brain and other parts of the nervous system, thyroid, Hodgkin's disease, non-Hodgkin's lymphoma, multiple myeloma and leukemia.

Examples of antigens that may be delivered alone or in combination to immune cells for antigen presentation using the present invention include tumor proteins, e.g., mutated oncogenes; viral proteins associated with tumors; and tumor mucins and glycolipids. The antigens may be viral proteins associated with tumors would be those from the classes of viruses noted above. Certain antigens may be characteristic of tumors (one subset being proteins not usually expressed by a tumor precursor cell), or may be a protein which is normally expressed in a tumor precursor cell, but having a mutation characteristic of a tumor. Other antigens include mutant variant(s) of the normal protein having an altered activity or subcellular distribution, e.g., mutations of genes giving rise to tumor antigens.

Specific non-limiting examples of tumor antigens include: CEA, prostate specific antigen (PSA), HER-2/neu, BAGE, GAGE, MAGE 1-4, 6 and 12, MUC (Mucin) (e.g., MUC-1, MUC-2, etc.), GM2 and GD2 gangliosides, ras, myc, tyrosinase, MART (melanoma antigen), Pmel 17(gp 100), GnT-V intron V sequence (N-acetylglucoaminyltransferase V intron V sequence), Prostate Ca psm, PRAME (melanoma antigen), β-catenin, MUM-1-B (melanoma ubiquitous mutated gene product), GAGE (melanoma antigen) 1, BAGE (melanoma antigen) 2-10, c-ERB2 (Her2/neu), EBNA (Epstein-Barr Virus nuclear antigen) 1-6, gp75, human papilloma virus (HPV) E6 and E7, p53, lung resistance protein (LRP), Bcl-2, and Ki-67. In addition, the immunogenic molecule can be an autoantigen involved in the initiation and/or propagation of an autoimmune disease, the pathology of which is largely due to the activity of antibodies specific for a molecule expressed by the relevant target organ, tissue, or cells, e.g., SLE or MG. In such diseases, it can be desirable to direct an ongoing antibody-mediated (i.e., a Th2-type) immune response to the relevant autoantigen towards a cellular (i.e., a Th1-type) immune response. Alternatively, it can be desirable to prevent onset of or decrease the level of a Th2 response to the autoantigen in a subject not having, but who is suspected of being susceptible to, the relevant autoimmune disease by prophylactically inducing a Th1 response to the appropriate autoantigen. Autoantigens of interest include, without limitation: (a) with respect to SLE, the Smith protein, RNP ribonucleoprotein, and the SS-A and SS-B proteins; and (b) with respect to MG, the acetylcholine receptor. Examples of other miscellaneous antigens involved in one or more types of autoimmune response include, e.g., endogenous hormones such as luteinizing hormone, follicular stimulating hormone, testosterone, growth hormone, prolactin, and other hormones.

Antigens involved in autoimmune diseases, allergy, and graft rejection can be used in the compositions and methods of the invention. For example, an antigen involved in any one or more of the following autoimmune diseases or disorders can be used in the present invention: diabetes, diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjogren's Syndrome, including keratoconjunctivitis sicca secondary to Sjogren's Syndrome, alopecia greata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves opthalmopathy, sarcoidosis, primary biliary cirrhosis, uveitis posterior, and interstitial lung fibrosis. Examples of antigens involved in autoimmune disease include glutamic acid decarboxylase 65 (GAD 65), native DNA, myelin basic protein, myelin proteolipid protein, acetylcholine receptor components, thyroglobulin, and the thyroid stimulating hormone (TSH) receptor. Examples of antigens involved in allergy include pollen antigens such as Japanese cedar pollen antigens, ragweed pollen antigens, rye grass pollen antigens, animal derived antigens such as dust mite antigens and feline antigens, histocompatiblity antigens, and penicillin and other therapeutic drugs. Examples of antigens involved in graft rejection include antigenic components of the graft to be transplanted into the graft recipient such as heart, lung, liver, pancreas, kidney, and neural graft components. The antigen may be an altered peptide ligand useful in treating an autoimmune disease.

As used herein, the term "epitope(s)" refer to a peptide or protein antigen that includes a primary, secondary or tertiary structure similar to an epitope located within any of a number of pathogen polypeptides encoded by the pathogen DNA or RNA. The level of similarity will generally be to such a degree that monoclonal or polyclonal antibodies directed against such polypeptides will also bind to, react with, or otherwise recognize, the peptide or protein antigen. Various immunoassay methods may be employed in conjunction with such antibodies, such as, for example, Western blotting, ELISA, RIA, and the like, all of which are known to those of skill in the art. The identification of pathogen epitopes, and/or their functional equivalents, suitable for use in vaccines is part of the present invention. Once isolated and identified, one may readily obtain functional equivalents. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, for example, Jameson and Wolf, 1988; Wolf et al., 1988; U.S. Pat. No. 4,554,101). The amino acid sequence of these "epitopic core sequences" may then be readily incorporated into peptides, either through the application of peptide synthesis or recombinant technology.

The preparation of vaccine compositions that includes the nucleic acids that encode antigens of the invention as the active ingredient, may be prepared as injectables, either as liquid solutions or suspensions; solid forms suitable for solution in, or suspension in, liquid prior to infection can also be prepared. The preparation may be emulsified, encapsulated in liposomes. The active immunogenic ingredients are often mixed with carriers which are pharmaceutically acceptable and compatible with the active ingredient.

The term "pharmaceutically acceptable carrier" refers to a carrier that does not cause an allergic reaction or other untoward effect in subjects to whom it is administered. Suitable pharmaceutically acceptable carriers include, for example, one or more of water, saline, phosphate buffered saline, dextrose, glycerol, ethanol, or the like and combinations thereof. In addition, if desired, the vaccine can contain minor amounts of auxiliary substances such as wetting or emulsifying agents, pH buffering agents, and/or adjuvants which enhance the effectiveness of the vaccine. Examples of adjuvants that may be effective include but are not limited to: aluminum hydroxide, N-acetyl-muramyl-L-threonyl-D-isoglutamine (thr-MDP), N-acetyl-nor-muramyl-L-alanyl-D-isoglutamine, MTP-PE and RIBI, which contains three components extracted from bacteria, monophosphoryl lipid A, trehalose dimycolate and cell wall skeleton (MPL+TDM+CWS) in a 2% squalene/Tween 80 emulsion. Other examples of adjuvants include DDA (dimethyldioctadecylammonium bromide), Freund's complete and incomplete adjuvants and QuilA. In addition, immune modulating substances such as lymphokines (e.g., IFN-γ, IL-2 and IL-12) or synthetic IFN-γ inducers such as poly I:C can be used in combination with adjuvants described herein.

Pharmaceutical products that may include a naked polynucleotide with a single or multiple copies of the specific nucleotide sequences that bind to specific DNA-binding sites of the apolipoproteins present on plasma lipoproteins as described in the current invention. The polynucleotide may encode a biologically active peptide, antisense RNA, or ribozyme and will be provided in a physiologically acceptable administrable form. Another pharmaceutical product that may spring from the current invention may include a highly purified plasma lipoprotein fraction, isolated according to the methodology, described herein from either the patients blood or other source, and a polynucleotide containing single or multiple copies of the specific nucleotide sequences that bind to specific DNA-binding sites of the apolipoproteins present on plasma lipoproteins, prebound to the purified lipoprotein fraction in a physiologically acceptable, administrable form.

Yet another pharmaceutical product may include a highly purified plasma lipoprotein fraction which contains recombinant apolipoprotein fragments containing single or multiple copies of specific DNA-binding motifs, prebound to a polynucleotide containing single or multiple copies of the specific nucleotide sequences, in a physiologically acceptable administrable form. Yet another pharmaceutical product may include a highly purified plasma lipoprotein fraction which contains recombinant apolipoprotein fragments containing single or multiple copies of specific DNA-binding motifs, prebound to a polynucleotide containing single or multiple copies of the specific nucleotide sequences, in a physiologically acceptable administrable form.

The dosage to be administered depends to a great extent on the body weight and physical condition of the subject being treated as well as the route of administration and frequency of treatment. A pharmaceutical composition that includes the naked polynucleotide prebound to a highly purified lipoprotein fraction may be administered in amounts ranging from 1 µg to 1 mg polynucleotide and 1 µg to 100 mg protein.

Administration of rAb and rAb complexes a patient will follow general protocols for the administration of chemotherapeutics, taking into account the toxicity, if any, of the vector. It is anticipated that the treatment cycles would be repeated as necessary. It also is contemplated that various standard therapies, as well as surgical intervention, may be applied in combination with the described gene therapy.

Where clinical application of a gene therapy is contemplated, it will be necessary to prepare the complex as a pharmaceutical composition appropriate for the intended application. Generally this will entail preparing a pharmaceutical composition that is essentially free of pyrogens, as well as any other impurities that could be harmful to humans or animals. One also will generally desire to employ appropriate salts and buffers to render the complex stable and allow for complex uptake by target cells.

Aqueous compositions of the present invention may include an effective amount of the compound, dissolved or dispersed in a pharmaceutically acceptable carrier or aqueous medium. Such compositions can also be referred to as inocula. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions. The compositions of the present invention may include classic pharmaceutical preparations. Dispersions also can be prepared in glycerol, liquid polyethylene glycols, and mixtures thereof and in oils. Under ordinary conditions of storage and use, these preparations contain a preservative to prevent the growth of microorganisms.

Disease States. Depending on the particular disease to be treated, administration of therapeutic compositions according to the present invention will be via any common route so long as the target tissue is available via that route in order to maximize the delivery of antigen to a site for maximum (or in some cases minimum) immune response. Administration will generally be by orthotopic, intradermal, subcutaneous, intramuscular, intraperitoneal or intravenous injection. Other areas for delivery include: oral, nasal, buccal, rectal, vaginal or topical. Topical administration would be particularly advantageous for treatment of skin cancers. Such compositions would normally be administered as pharmaceutically acceptable compositions that include physiologically acceptable carriers, buffers or other excipients.

Vaccine or treatment compositions of the invention may be administered parenterally, by injection, for example, either subcutaneously or intramuscularly. Additional formulations which are suitable for other modes of administration include suppositories, and in some cases, oral formulations or formulations suitable for distribution as aerosols. In the case of the oral formulations, the manipulation of T-cell subsets employing adjuvants, antigen packaging, or the addition of individual cytokines to various formulation that result in improved oral vaccines with optimized immune responses. For suppositories, traditional binders and carriers may include, for example, polyalkylene glycols or triglycerides; such suppositories may be formed from mixtures containing the active ingredient in the range of 0.5% to 10%, preferably 1%-2%. Oral formulations include such normally employed excipients as, for example, pharmaceutical grades of mannitol, lactose, starch magnesium stearate, sodium saccharine, cellulose, magnesium carbonate, and the like. These compositions take the form of solutions, suspensions, tablets, pills, capsules, sustained release formulations or powders and contain 10%-95% of active ingredient, preferably 25-70%.

The antigen encoding nucleic acids of the invention may be formulated into the vaccine or treatment compositions as neutral or salt forms. Pharmaceutically acceptable salts include the acid addition salts (formed with free amino groups of the peptide) and which are formed with inorganic acids such as, for example, hydrochloric or phosphoric acids, or with organic acids such as acetic, oxalic, tartaric, maleic, and the like. Salts formed with the free carboxyl groups can also be derived from inorganic bases such as, for example, sodium, potassium, ammonium, calcium, or ferric hydroides, and such organic bases as isopropylamine, trimethylamine, 2-ethylamino ethanol, histidine, procaine, and the like.

Vaccine or treatment compositions are administered in a manner compatible with the dosage formulation, and in such amount as will be prophylactically and/or therapeutically effective. The quantity to be administered depends on the subject to be treated, including, e.g., capacity of the subject's immune system to synthesize antibodies, and the degree of protection or treatment desired. Suitable dosage ranges are of the order of several hundred micrograms active ingredient per vaccination with a range from about 0.1 mg to 1000 mg, such as in the range from about 1 mg to 300 mg, and preferably in the range from about 10 mg to 50 mg. Suitable regiments for initial administration and booster shots are also variable but are typified by an initial administration followed by subsequent inoculations or other administrations. Precise amounts of active ingredient required to be administered depend on the judgment of the practitioner and may be peculiar to each subject. It will be apparent to those of skill in the art that the therapeutically effective amount of nucleic acid molecule or fusion polypeptides of this invention will depend, inter alia, upon the administration schedule, the unit dose of antigen administered, whether the nucleic acid molecule or fusion polypeptide is administered in combination with other therapeutic agents, the immune status and health of the recipient, and the therapeutic activity of the particular nucleic acid molecule or fusion polypeptide.

The compositions can be given in a single dose schedule or in a multiple dose schedule. A multiple dose schedule is one in which a primary course of vaccination may include, e.g., 1-10 separate doses, followed by other doses given at subsequent time intervals required to maintain and or reinforce the immune response, for example, at 1-4 months for a second dose, and if needed, a subsequent dose(s) after several months. Periodic boosters at intervals of 1-5 years, usually 3 years, are desirable to maintain the desired levels of protective immunity. The course of the immunization can be followed by in vitro proliferation assays of peripheral blood lymphocytes (PBLs) co-cultured with ESAT6 or ST-CF, and by measuring the levels of IFN-γ released from the primed lymphocytes. The assays may be performed using conventional labels, such as radionucleotides, enzymes, fluorescent labels and the like. These techniques are known to one skilled in the art and can be found in U.S. Pat. Nos. 3,791,932, 4,174,384 and 3,949,064, relevant portions incorporated by reference.

The modular rAb carrier and/or conjugated rAb carrier-(cohesion/dockerin and/or dockerin-cohesin)-antigen complex (rAb-DC/DC-antigen vaccine) may be provided in one or more "unit doses" depending on whether the nucleic acid vectors are used, the final purified proteins, or the final vaccine form is used. Unit dose is defined as containing a predetermined-quantity of the therapeutic composition calculated to produce the desired responses in association with its administration, i.e., the appropriate route and treatment regimen. The quantity to be administered, and the particular route and formulation, are within the skill of those in the clinical arts. The subject to be treated may also be evaluated, in particular, the state of the subject's immune system and the protection desired. A unit dose need not be administered as a single injection but may include continuous infusion over a set period of time. Unit dose of the present invention may conveniently may be described in terms of DNA/kg (or protein/Kg) body weight, with ranges between about 0.05, 0.10, 0.15, 0.20, 0.25, 0.5, 1, 10, 50, 100, 1,000 or more mg/DNA or protein/kg body weight are administered. Likewise the amount of rAb-DC/DC-antigen vaccine delivered can vary from about 0.2 to about 8.0 mg/kg body weight. Thus, in particular embodiments, 0.4 mg, 0.5 mg, 0.8 mg, 1.0 mg, 1.5 mg, 2.0 mg, 2.5 mg, 3.0 mg, 4.0 mg, 5.0 mg, 5.5 mg, 6.0 mg, 6.5 mg, 7.0 mg and 7.5 mg of the vaccine may be delivered to an individual in vivo. The dosage of rAb-DC/DC-antigen vaccine to be administered depends to a great extent on the weight and physical condition of the subject being treated as well as the route of administration and the frequency of treatment. A pharmaceutical composition that includes a naked polynucleotide prebound to a liposomal or viral delivery vector may be administered in amounts ranging from 1 µg to 1 mg polynucleotide to 1 µg to 100 mg protein. Thus, particular compositions may include between about 1 µg, 5 µg, 10 µg, 20 µg, 30 µg, 40 µg, 50 µg, 60 µg, 70 µg, 80 µg, 100 µg, 150 µg, 200 µg, 250 µg, 500 µg, 600 µg, 700 µg, 800 µg, 900 µg or 1,000 µg polynucleotide or protein that is bound independently to 1 µg, 5 µg, 10 µg, 20 µg, 3.0 µg, 40 µg 50 µg, 60 µg, 70 µg, 80 µg, 100 µg, 150 µg, 200 µg, 250 µg, 500 µg, 600 µg, 700 µg, 800 µg, 900 µg, 1 mg, 1.5 mg, 5 mg, 10 mg, 20 mg, 30 mg, 40 mg, 50 mg, 60 mg, 70 mg, 80 mg, 90 mg or 100 mg vector.

The present invention was tested in an in vitro cellular system that measures immune stimulation of human Flu-specific T cells by dendritic cells to which Flu antigen has been targeted. The results shown herein demonstrate the specific expansion of such antigen specific cells at doses of the antigen which are by themselves ineffective in this system.

The present invention may also be used to make a modular rAb carrier that is, e.g., a recombinant humanized mAb (directed to a specific human dendritic cell receptor) complexed with protective antigens from Ricin, Anthrax toxin, and *Staphylococcus* B enterotoxin. The potential market for this entity is vaccination of all military personnel and stored vaccine held in reserve to administer to large population centers in response to any biothreat related to these agents. The invention has broad application to the design of vaccines in general, both for human and animal use. Industries of interest include the pharmaceutical and biotechnology industries.

The present invention includes compositions and methods, including vaccines, that specifically target (deliver) antigens to antigen-presenting cells (APCs) for the purpose of eliciting potent and broad immune responses directed against the antigen. These compositions evoke protective or therapeutic immune responses against the agent (pathogen or cancer) from which the antigen was derived. In addition the invention creates agents that are directly, or in concert with other agents, therapeutic through their specific engagement of the LOX-1 receptor expressed on antigen-presenting cells.

Materials and Methods.

Antibodies and tetramers—Antibodies (Abs) for surface staining of DCs and B cells, including isotype control Abs, were purchased from BD Biosciences (CA). Abs for ELISA were purchased from Bethyl (TX). Anti-BLyS and anti-APRIL were from PeproTech (NJ). Tetramers, HLA-A*0201-GILGFVFTL (Flu M1) and HLA-A*0201-ELAGIGILTV (Mart-1), were purchased from Beckman Coulter (CA).

Cells and cultures—Monocytes ($1 \times 10^6$/ml) from normal donors were cultured in Cellgenics (France) media containing GM-CSF (100 ng/ml) and IL-4 (50 ng/ml) (R&D, CA). For day three and day six, DCs, the same amounts of cytokines were supplemented into the media on day one and day three, respectively. B cells were purified with a negative isolation kit (BD). CD4 and CD8 T cells were purified with magnetic beads coated with anti-CD4 or CD8 (Milteniy, CA). PBMCs were isolated from Buffy coats using Percoll™ gradients (GE Healthcare UK Ltd, Buckinghamshire, UK) by density gradient centrifugation. For DC activation, $1 \times 10^5$ DCs were cultured in the mAb-coated 96-well plate for 16-18 h. mAbs (1-2 ug/well) in carbonate buffer, pH 9.4, were incubated for at least 3 h at 37° C. Culture supernatants were harvested and cytokines/chemokines were measured by Luminex (Biorad, CA). For gene analysis, DCs were cultured in the plates coated with mAbs for 8 h. In some experiments, soluble 50 ng/ml of CD40L (R&D, CA) or 50 nM CpG (InVivogen, CA) was added into the cultures. In the DCs and B cell co-cultures, $5 \times 10^3$ DCs resuspended in RPMI 1640 with 10% FCS and antibiotics (Biosource, C A) were first cultured in the plates coated with mAbs for at least 6 h, and then $1 \times 10^5$ purified autologous B cells labeled with CFSE (Molecular Probes, OR) were added. In some experiments, DCs were pulsed with 5 moi (multiplicity of infection) of heat-inactivated influenza virus (A/PR/8 H1N1) for 2 h, and then mixed with B cells. For the DCs and T cell co-cultures, $5 \times 10^3$ DCs were cultured with $1 \times 10^5$ purified autologous CD8 T cells or mixed allogeneic T cells. Allogeneic T cells were pulsed with 1 uCi/well $^3$[H]-thymidine for the final 18 h of incubation, and then cpm were measured by a gamma-counter (Wallac, Minn.). $5 \times 10^5$ PBMCs/well were cultured in the plates coated with mAbs. The frequency of Mart-1 and Flu M1 specific CD8 T cells was measured by staining cells with anti-CD8 and tetramers on day ten and day seven of the cultures, respectively. 10 uM of Mart-1 peptide (ELAGIGILTV) and 20 nM of recombinant protein containing Mart-1 peptides (see below) were added to the DC and CD8 T cell cultures. 20 nM purified recombinant Flu M1 protein (see below) was add to the PBMC cultures.

Monoclonal antibodies—Mouse mAbs were generated by conventional technology. Briefly, six-week-old BALB/c mice were immunized i.p. with 20 µg of receptor ectodomain.hIgGFc fusion protein with Ribi adjuvant, then boosts with 20 µg antigen ten days and fifteen days later. After three months, the mice were boosted again three days prior to taking the spleens. Alternately, mice were injected in the footpad with 1-10 µg antigen in Ribi adjuvant every three to four days over a thirty to forty day period. Three to four days after a final boost, draining lymph nodes were harvested. B cells from spleen or lymph node cells were fused with SP2/O—Ag 14 cells. Hybridoma supernatants were screened to analyze Abs to the receptor ectodomain fusion protein compared to the fusion partner alone, or the receptor ectodomain fused to alkaline phosphatase (16). Positive wells were then screened in FACS using 293F cells transiently transfected with expression plasmids encoding full-length receptor cDNAs. Selected hybridomas were single cell cloned and expanded in CEL-Line flasks (Integra, CA). Hybridoma supernatants were mixed with an equal volume of 1.5 M glycine, 3 M NaCl, 1×PBS, pH 7.8 and tumbled with MabSelect resin. The resin was washed with binding buffer and eluted with 0.1 M glycine, pH 2.7. Following neutralization with 2 M Tris, mAbs were dialyzed versus PBS.

ELISA—Sandwich ELISA was performed to measure total IgM, IgG, and IgA as well as flu-specific immunoglobulins (Igs). Standard human serum (Bethyl) containing known amounts of Igs and human AB serum were used as standard for total Igs and flu-specific Igs, respectively. Flu specific Ab titers, units, in samples were defined as dilution factor of AB serum that shows an identical optical density. The amounts of BAFF and BLyS were measured by ELISA kits (Bender MedSystem, CA).

RNA purification and gene analysis—Total RNA extracted with RNeasy columns (Qiagen), and analyzed with the 2100 Bioanalyser (Agilent). Biotin-labeled cRNA targets were prepared using the Illumina totalprep labeling kit (Ambion) and hybridized to Sentrix Human6 BeadChips (46K transcripts). These microarrays consist of 50 mer oligonucleotide probes attached to 3 um beads which are lodged into microwells etched at the surface of a silicon wafer. After staining with Streptavidin-Cy3, the array surface is imaged using a submicron resolution scanner manufactured by Illumina (Beadstation 500×). A gene expression analysis software program, GeneSpring, Version 7.1 (Agilent), was used to perform data analysis.

Expression and purification of recombinant Flu M1 and MART-1 proteins—PCR was used to amplify the ORF of Influenza A/Puerto Rico/8/34/Mount Sinai (H1N1) M1 gene while incorporating an Nhe I site distal to the initiator codon and a Not I site distal to the stop codon. The digested fragment was cloned into pET28b(+) (Novagen), placing the M1 ORF in-frame with a His6 tag, thus encoding His.Flu M1 protein. A pET28b (+) derivative encoding an N-terminal 169 residue cohesin domain from *C. thermocellum* (unpublished) inserted between the Nco I and Nhe I sites expressed Coh.His. For expression of Cohesin-Flex-hMART-1-PeptideA-His, the sequence GACACCACCGAGGCCCGCCACCCCCAC-CCCCCCGTGACCACCCCCACCACCACCGA CCG-GAAGGGCACCACCGCCGAGGAGCTGGC-CGGCATCGGCATCCTGACCGTGATCC TGGGCGGCAAGCGGACCAACAACAGCAC-CCCCACCAAGGGCGAATTCTGCAGATA TCCATCA-CACTGGCGGCCG (SEQ ID NO.: 1)(encoding DTTEAR-HPHPPVTTPTTDRKGTTAEELAGIGILTV ILGGKRTNNSTPTKGEFCRYPSHWRP (SEQ ID NO.: 2)—the shaded residues are the immuno-dominant HLA-A2-restricted peptide and the underlined residues surrounding the peptide are from MART-1) was inserted between the Nhe I and Xho I sites of the above vector. The proteins were expressed in *E. coli* strain BL21 (DE3) (Novagen) or T7 Express (NEB), grown in LB at 37° C. with selection for kanamycin resistance (40 µg/ml) and shaking at 200 rounds/min to mid log phase growth when 120 mg/L IPTG was added. After three hours, the cells were harvested by centrifugation and stored at −80° C. *E. coli* cells from each 1 L fermentation were resuspended in 30 ml ice-cold 50 mM Tris, 1 mM EDTA pH 8.0 (buffer B) with 0.1 ml of protease inhibitor Cocktail II (Calbiochem, CA). The cells were sonicated on ice 2× 5 min at setting 18 (Fisher Sonic Dismembrator 60) with a 5 min rest period and then spun at 17,000 r.p.m. (Sorvall SA-600) for 20 min at 4° C. For His.Flu M1 purification the 50 ml cell lysate supernatant fraction was passed through 5 ml Q Sepharose beads and 6.25 ml 160 mM Tris, 40 mM imidazole, 4 M NaCl pH 7.9 was added to the Q Sepharose flow through. This was loaded at 4 ml/min onto a 5 ml HiTrap chelating HP column charged with Ni++. The column-bound protein was washed with 20 mM NaPO$_4$, 300 mM NaCl pH 7.6 (buffer D) followed by another wash with 100 mM H$_3$COONa pH 4.0. Bound protein was eluted with 100 mM H$_3$COONa pH 4.0. The peak fractions were pooled and loaded at 4 ml/min onto a 5 ml HiTrap S column equilibrated with 100 mM H$_3$COONa pH 5.5, and washed with the equilibration buffer followed by elution with a gradient from 0-1 M NaCl in 50 mM NaPO$_4$ pH 5.5. Peak fractions eluting at about 500 mM NaCl were pooled. For Coh.Flu M1.His purification, cells from 2 L of culture were lysed as above. After centrifugation, 2.5 ml of Triton X114 was added to the supernatant with incubation on ice for 5 min. After further incubation at 25° C. for 5 min, the supernatant was separated from the Triton X114 following centrifugation at 25° C. The extraction was repeated and the supernatant was passed through 5 ml of Q Sepharose beads and 6.25 ml 160 mM Tris, 40 mM imidazole, 4 M NaCl pH 7.9 was added to the Q Sepharose flow through. The protein was then purified by Ni$^{++}$ chelating chromatography as described above and eluted with 0-500 mM imidazole in buffer D.

Anti-LOX-1 mAbs—The invention encompasses particular amino acid sequences shown below corresponding to anti-LOX-1 monoclonal antibodies that are desirable components (in the context of e.g., humanized recombinant antibodies) of therapeutic or protective products. The following are such sequences in the context of chimeric mouse V region (underlined) human C region recombinant antibodies. These mouse V regions can be readily 'humanized, i.e., the LOX-1 combining regions grafted onto human V region framework sequences, by anyone well practiced in this art. Furthermore, the sequences can also be expressed in the context of fusion proteins that preserve antibody functionality, but add e.g., antigen, cytokine, or toxin for desired therapeutic applications.

[mAnti-LOX-1_11C8H-LV-hIgG4H-C]
(SEQ ID NO.: 3)
EVQLQQSGTVLARPGASVKMSCKASGYTFTSYWMHWVKQRPGQGLEWIGA

IYPGNSDTTYNQKFKGKAKLTAVTSTSTAYMELSSLTNEDSAVYYCTPTY

YFDYWGQGTSLTVSSAKTKGPSVFPLAPCSRSTSESTAALGCLVKDYFPE

PVTVSWNSGALTSGVHTFPAVLQSSGLYSLSSVVTVPSSSLGTKTYTCNV

DHKPSNTKVDKRVESKYGPPCPPCPAPEFEGGPSVFLFPPKPKDTLMISR

TPEVTCVVVDVSQEDPEVQFNWYVDGVEVHNAKTKPREEQFNSTYRVVSV

LTVLHQDWLNGKEYKCKVSNKGLPSSIEKTISKAKGQPREPQVYTLPPSQ

EEMTKNQVSLTCLVKGFYPSDIAVEWESNGQPENNYKTTPPVLDSDGSFF

LYSRLTVDKSRWQEGNVFSCSVMHEALHNHYTQKSLSLSLGKAS

[mAnti-LOX-1_11C8K-LV-hIgGK-C]
(SEQ ID NO.: 4)
DVVMTQTPLTLSVTIGQPASISCKSSQSLLDSDGKTYLNWFLQRPGQSPK

RLIYLVSKLDSGVPDRFTGSGSGTDFTLKISRVEAEDLGVYYCWQGTHFP

WTFGGGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

[mAnti-LOX_1_10F9H-LV-hIgG4H-C]
(SEQ ID NO.: 5)
QVQLQQSGAELMKPGASVKISCKATGYTFGSYWIEWVKQRPGHGLEWIGE

ILPGSGNTNYNENFKGKATFTADTSSNTAYMQLTSLTSEDSAVYYCARAG

-continued

IYWGQGTLVTVSAAKTKGPSVFPLAPCSRSTSESTAALGCLVKDYFPEPV

TVSWNSGALTSGVHTFPAVLQSSGLYSLSSVVTVPSSSLGTKTYTCNVDH

KPSNTKVDKRVESKYGPPCPPCPAPEFEGGPSVFLFPPKPKDTLMISRTP

EVTCVVVDVSQEDPEVQFNWYVDGVEVHNAKTKPREEQFNSTYRVVSVLT

VLHQDWLNGKEYKCKVSNKGLPSSIEKTISKAKGQPREPQVYTLPPSQEE

MTKNQVSLTCLVKGFYPSDIAVEWESNGQPENNYKTTPPVLDSDGSFFLY

SRLTVDKSRWQEGNVFSCSVMHEALHNHYTQKSLSLSLGKAS

[mAnti-LOX_1_10F9K-LV-hIgGK-C]

(SEQ ID NO.: 6)
DIVLTQSPAFLAVSLGQRATISCRASESVDNYGISFMNWFQQKPGQPPKL

LIYVASKQGSGVPARFSGSGSGTDFSLNIHPMEEDDTAMYFCQQSKEVPR

TFGGGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC

[mAnti-LOX-1_15C4H-LV-hIgG4H-C]

(SEQ ID NO.: 7)
EIQLQQTGPELVKPGASVKISCKASGYPFTDYIMVWVKQSHGKSLEWIGN

ISPYYGTTNYNLKFKGKATLTVDKSSSTAYMQLNSLTSEDSAVYYCARSP

NWDGAWFAHWGQGALVTVSAAKTKGPSVFPLAPCSRSTSESTAALGCLVK

DYFPEPVTVSWNSGALTSGVHTFPAVLQSSGLYSLSSVVTVPSSSLGTKT

YTCNVDHKPSNTKVDKRVESKYGPPCPPCPAPEFEGGPSVFLFPPKPKDT

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGKAS

[mAnti-LOX-1_15C4K-LV-hIgGK-C]

(SEQ ID NO.: 8)
DIVLTQSPASLAVSLGQRATISCKASQSVDYDGDSYMNWFQQKPGQPPKL

LIYAASNLESGIPARFSGSGSGTDFTLNIHPVEEEDAATYYCQQSNEDPF

TFGSGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC

The present invention includes V-region sequences and related sequences modified by those well versed in the art to e.g., enhance affinity for LOX-1 and/or integrated into human V-region framework sequences to be engineered into expression vectors to direct the expression of protein forms that can bind to LOX-1 on antigen presenting cells. Furthermore, the other mAbs disclosed in the invention (or derived using similar methods and screens for the unique biology disclosed herein), can be via similar means (initially via PCR cloning and sequencing of mouse hybridoma V regions) be rendered into expression constructs encoding similar recombinant antibodies (rAbs). Such anti-LOX-1 V regions can furthermore, by those well versed in the art, be 'humanized (i.e., mouse-specific combining sequences grafted onto human V region framework sequences) so as to minimize potential immune reactivity of the therapeutic rAb.

Engineered recombinant anti-LOX-1 recombinant antibody—antigen fusion proteins ((rAb.antigen) are efficacious prototype vaccines in vitro—Expression vectors can be constructed with diverse protein coding sequence e.g., fused in-frame to the H chain coding sequence. For example, antigens such as Influenza HA5, Influenza M1, HIV gag, or immuno-dominant peptides from cancer antigens, or cytokines, can be expressed subsequently as rAb.antigen or rAb.cytokine fusion proteins, which in the context of this invention, can have utility derived from using the anti-LOX-1 V-region sequence to bring the antigen or cytokine (or toxin) directly to the surface of the antigen presenting cell bearing LOX-1. This permits internalization of e.g., antigen—sometimes associated with activation of the receptor and ensuing initiation of therapeutic or protective action (e.g., via initiation of a potent immune response, or via killing of the targeted cell. An exemplative prototype vaccine based on this concept could use a H chain vector such as rAB-pIRES2[mAnti-LOX-1__15C4H-LV-hIgG4H-C-Flex-FluHA5-1-6×His] which directs the synthesis of a H chain mouse mAb V region (underlined)—human IgG4 C region—Flu HA5-1 (bold) fusion protein. Co-expressed with the analogous light chain expression plasmid (encoding sequence shown above), this produces a multifunctional recombinant antibody (rAb) that binds LOX-1 and delivers Flu HA5-1 antigen to the cell surface for DC activation, antigen internalization, antigen processing, antigen presentation, and education and expansion of specific anti-Flu HA5-1 B and T cells.

(SEQ ID NO.: 9)
EIQLQQTGPELVKPGASVKISCKASGYPFTDYIMVWVKQSHGKSLEWIGN

ISPYYGTTNYNLKFKGKATLTVDKSSSTAYMQLNSLTSEDSAVYYCARSP

NWDGAWFAHWGQGALVTVSAAKTKGPSVFPLAPCSRSTSESTAALGCLVK

DYFPEPVTVSWNSGALTSGVHTFPAVLQSSGLYSLSSVVTVPSSSLGTKT

YTCNVDHKPSNTKVDKRVESKYGPPCPPCPAPEFEGGPSVFLFPPKPKDT

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGKASD

TTEPATPTTPVTTDQICIGYHANNSTEQVDTIMEKNVTVTHAQDILEKKH

NGKLCDLDGVKPLILRDCSVAGWLLGNPMCDEFINVPEWSYIVEKANPVN

DLCYPGDFNDYEELKHLLSRINHFEKIQIIPKSSWSSHEASLGVSSACPY

QGKSSFFRNVVWLIKKNSTYPTIKRSYNNTNQEDLLVLWGIHHPNDAAEQ

TKLYQNPTTYISVGTSTLNQRLVPRIATRSKVNGQSGRMEFFWTILKPND

AINFESNGNFIAPEYAYKIVKKGDSTIMKSELEYGNCNTKCQTPMGAINS

SMPFHNIHPLTIGECPKYVKSNRLVLAHHHHHH

Similarly, rAB-pIRES2[mAnti-LOX-1__15C4H-LV-hIgG4H-C-Dockerin] encodes an anti-LOX-1H chain fused to dockerin (sequence shown below). The dockerin allows for strong specific non-covalent interaction with cohesin-antigen (coh.antigen) fusion proteins—providing an alternate means of delivering antigen to DC and other antigen presenting cells.

(SEQ ID NO.: 10)
EIQLQQTGPELVKPGASVKISCKASGYPFTDYIMVWVKQSHGKSLEWIGN

ISPYYGTTNYNLKFKGKATLTVDKSSSTAYMQLNSLTSEDSAVYYCARSP

NWDGAWFAHWGQGALVTVSAAKTKGPSVFPLAPCSRSTSESTAALGCLVK

-continued

DYFPEPVTVSWNSGALTSGVHTFPAVLQSSGLYSLSSVVTVPSSSLGTKT

YTCNVDHKPSNTKVDKRVESKYGPPCPPCPAPEFEGGPSVFLFPPKPKDT

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGKASN

SPQNEVLYGDVNDDGKVNSTDLTLLKRYVLKAVSTLPSSKAEKNADVNRD

GRVNSSDVTILSRYLIRVIEKLPI

(SEQ ID NO.: 11)
<u>EIQLQQTGPELVKPGASVKISCKASGYPFTDYIMVWVKQSHGKSLEWIGN</u>

<u>ISPYYGTTNYNLKFKGKATLTVDKSSSTAYMQLNSLTSEDSAVYYCARSP</u>

<u>NWDGAWFAHWGQGALVTVSAAKTKGPSVFPLAPCSRSTSESTAALGCLVK</u>

DYFPEPVTVSWNSGALTSGVHTFPAVLQSSGLYSLSSVVTVPSSSLGTKT

YTCNVDHKPSNTKVDKRVESKYGPPCPPCPAPEFEGGPSVFLFPPKPKDT

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGKASD

TTEPATPTTPVTTPTTTLLAPLILSRIVGGWECEKHSQPWQVLVASRGRA

VCGGVLVHPQWVLTAAHCIRNKSVILLGRHSLFHPEDTGQVFQVSHSFPH

PLYDMSLLKNRFLRPGDDSSHDLMLLRLSEPAELTDAVKVMDLPTQEPAL

GTTCYASGWGSIEPEEFLTPKKLQCVDLHVISNDVCAQVHPQKVTKFMLC

AGRWTGGKSTCSGDSGGPLVCNGVLQGITSWGSEPCALPERPSLYTKVVH

YRKWIKDTIVANP

Methods Relating to Cloning and Expression of Recombinant Antibodies (rAbs) and rAb.Antigens cDNA cloning and expression of chimeric mouse/human mAbs—Total RNA was prepared from hybridoma cells (RNeasy kit, Qiagen) and used for cDNA synthesis and PCR (SMART RACE kit, BD Biosciences) using supplied 5' primers and gene specific 3' primers:

mIgGκ,
(SEQ ID NO.: 12)
5'ggatggtgggaagatggatacagttggtgcagcatc3';

mIgGλ,
(SEQ ID NO.: 13)
5'ctaggaacagtcagcacgggacaaactcttctccacagtgtgacct tc3';

mIgG1,
(SEQ ID NO.: 14)
5'gtcactggctcagggaaatagcccttgaccaggcatc3';

mIgG2a,
(SEQ ID NO.: 15)
5'ccaggcatcctagagtcaccgaggagccagt3';
and mIgG2b,
(SEQ ID NO.: 16)
5'ggtgctggaggggacagtcactgagctgctcatagtgt3'.

PCR products were cloned (pCR2.1 TA kit, Invitrogen) and characterized by DNA sequencing. Using the derived sequences for the mouse H and L chain V-region cDNAs, specific primers were used to PCR amplify the signal peptide and V-regions while incorporating flanking restriction sites for cloning into expression vectors encoding downstream human IgGκ or IgG4H regions. The vector for expression of chimeric mVκ-hIgκ was built by amplifying residues 401-731 (gi|63101937|) flanked by Xho I and Not I sites and inserting this into the Xho I-Not I interval of pIRES2-DsRed2 (BD Biosciences). PCR was used to amplify the mAb Vk region from the initiator codon, appending a Nhe I or Spe I site then CACC, to the region encoding (e.g., residue 126 of gi|76779294|), appending a Xho I site. The PCR fragment was then cloned into the Nhe I-Not I interval of the above vector. The vector for chimeric mVκ-hIgκ using the mSLAM leader was built by inserting the sequence 5'ctagttgctggctaatggaccccaaaggctcccttc-ctggagaatacttctgtttctctccctggcttttgagttgtcgtacggattaattaag ggcccactcgag3' (SEQ ID NO.: 17) into the Nhe I-Xho I interval of the above vector. PCR was used to amplify the interval between the predicted mature N-terminal codon (defined using the SignalP 3.0 Server) (Bendtsen, Nielsen et al. 2004) and the end of the mVκ region (as defined above) while appending 5'tcgtacgga3'. The fragment digested with Bsi WI and Xho I was inserted into the corresponding sites of the above vector. The control hIg sequence corresponds to gi|49257887| residues 26-85 and gi|21669402| residues 67-709. The control hIgG4H vector corresponds to residues 12-1473 of gi|19684072| with S229P and L236E substitutions, which stabilize a disulphide bond and abrogate residual FcR binding (Reddy, Kinney et al. 2000), inserted between the pIRES2-DsRed2 vector Bgl II and Not I sites while adding the sequence 5'gctagctgattaattaa3' instead of the stop codon. PCR was used to amplify the mAb VH region from the initiator codon, appending CACC then a Bgl II site, to the region encoding residue 473 of gi|19684072|. The PCR fragment was then cloned into the Bgl II-Apa I interval of the above vector. The vector for chimeric mVH-hIgG4 sequence using the mSLAM leader was built by inserting the sequence 5' ctagttgctggctaatggaccccaaag-gctcccttcctggagaatacttct-gtttctctccctggcttttgagttgtcgtacggattaattaag ggccc3' (SEQ ID NO.: 18) into the Nhe I-Apa I interval of the above vector. PCR was used to amplify the interval between the predicted mature N-terminal codon and the end of the mVH region while appending 5'tcgtacgga3'. The fragment digested with Bsi WI and Apa I was inserted into the corresponding sites of the above vector. Appendix 2 details the nucleotide sequences of the various mVκ and mVH regions used in this study.

Various antigen coding sequences flanked by a proximal Nhe I site and a distal Not I site following the stop codon were inserted into the Nhe I-Pac I-Not I interval of the H chain vectors. Flu HA1-1 was encoded by Influenza A virus (A/Puerto Rico/8/34(H1N1)) hemagglutinin gi|21693168| residues 82-1025 (with a C982T change) with proximal 5'gctagcgata-caacagaacctgcaacacctacaacacctgtaacaa3' sequence (a Nhe I site followed by sequence encoding cipA cohesin-cohesin linker residues) and distal 5'caccatcaccatcaccattgagcggccgc3' sequence (encoding His6, a stop codon, and a Not I site). Flu HA5-1 was encoded by gi|50296052| Influenza A virus (A/Viet Nam/1203/2004(H5N1)) hemagglutinin residues 49-990 bound by the same sequences as Flu HA1-1. Doc was encoded by gi|40671| celD residues 1923-2150 with proximal Nhe I and distal Not I sites. PSA was encoded by gi|34784812| prostate specific antigen residues 101-832 with proximal sequence 5' gctagcgatacaacagaacctgcaacacctacaacacctgtaacaacaccgacaacaacacttctagcgc3' (SEQ ID NO.: 19) (Nhe I site and cipA spacer) and a distal Not I site. Flu M1-PEP was encoded by 5' gctagccccattctgagccccctgaccaaaggcattctgggctttgtgtttaccctgaccgtgcccagcgaacgcaagggtatacttgga ttcgttttcacacttacttaagcggccgc3' (SEQ ID NO.: 20). This and all other peptide-encoding sequences were created via mixtures of complimentary synthetic DNA fragments with ends compatible for cloning into Nhe I and Not I-restricted H chain vectors, or Nhe I-Xho I-restricted Coh.His vector. Preferred human codons were always used, except where restriction sites needed to be incorporated or in CipA spacer sequences.

Production levels of rAb expression constructs were tested in 5 ml transient transfections using ~2.5 μg each of the L chain and H chain construct and the protocol described above. Supernatants were analyzed by anti-hIgG ELISA (AffiniPure Goat anti-human IgG (H+L), Jackson ImmunoResearch). In tests of this protocol, production of secreted rAb was independent of H chain and L chain vectors concentration over a ~2-fold range of each DNA concentration (i.e., the system was DNA saturated).

The present inventors demonstrate herein that LOX-1, one of the LLRs, is functional, either alone or in collaboration with other cellular signals, in terms of cell (including DC) activation. LOX-1-mediated cell activation is induced by particular anti-LOX-1 mAbs, and therefore such anti-human LOX-1 mAbs will be useful for developing reagents against diseases.

The present invention includes novel anti-human LOX-1 reagents and their use to discover novel biology that is the basis of the invention and its applications. In summary, novel anti-LOX-1 monoclonal antibodies (mAbs) were developed and used to uncover previously unknown biology associated with this cell surface receptor that is found on antigen-presenting cells. This novel biology is highly predictive of the application of anti-LOX-1 agents that activate this receptor for diverse therapeutic and protective applications. Data presented below strongly support the initial predictions and demonstrated the pathway to reducing the discoveries herein to clinical application.

Development of high affinity monoclonal antibodies against human LOX-1: Receptor ectodomain.hIgG (human IgG1Fc) and AP (human placental alkaline phosphatase) fusion proteins were produced for immunization of mice and screening of mAbs, respectively. An expression construct for DCIR ectodomain.IgG was described previously (16) and used the mouse SLAM (mSLAM) signal peptide to direct secretion (17). An expression vector for DCIR ectodomain.AP was also generated using PCR to amplify AP resides 133-1581 (gb|BC009647|) while adding a proximal in-frame Xho I site and a distal TGA stop codon and Not I site. This Xho I-Not I fragment replaced the IgG coding sequence in the above DCIR ectodomain.IgG vector. LOX-1 ectodomain constructs in the same Ig and AP vector series contained inserts encoding (bp 224-874, gi|184901521|). LOX-1 fusion proteins were produced using the FreeStyle™ 293 Expression System (Invitrogen) according to the manufacturer's protocol (1 mg total plasmid DNA with 1.3 ml 293 Fectin reagent/L of transfection). For rAb production, equal amounts of vector encoding the H and L chain were co-transfected. Transfected cells are cultured for 3 days, the culture supernatant was harvested and fresh media added with continued incubation for two days. The pooled supernatants were clarified by filtration. Receptor ectodomain.hIgG was purified by HiTrap protein A affinity chromatography with elution by 0.1 M glycine pH 2.7 and then dialyzed versus PBS. rAbs (recombinant antibodies described later) were purified similarly, by using HiTrap MabSelect™ columns. Mouse mAbs were generated by conventional cell fusion technology. Briefly, 6-week-old BALB/c mice were immunized intraperitonealy with 20 μg of receptor ectodomain-.hIgGFc fusion protein with Ribi adjuvant, then boosts with 20 μg antigen 10 days and 15 days later. After 3 months, the mice were boosted again three days prior to taking the spleens. Alternately, mice were injected in the footpad with 1-10 μg antigen in Ribi adjuvant every 3-4 days over a 30-40 day period. 3-4 days after a final boost, draining lymph nodes were harvested. B cells from spleen or lymph node cells were fused with SP2/O—Ag 14 cells (18) using conventional techniques. ELISA was used to screen hybridoma supernatants against the receptor ectodomain fusion protein compared to the fusion partner alone, or versus the receptor ectodomain fused to AP (16). Positive wells were then screened in FACS using 293F cells transiently transfected with expression plasmids encoding full-length receptor cDNAs. Selected hybridomas were single cell cloned, adapted to serum-free media, and expanded in CELLine flasks (Intergra). Hybridoma supernatants were mixed with an equal volume of 1.5 M glycine, 3 M NaCl, 1×PBS, pH 7.8 and tumbled with Mab-Select resin. The resin was washed with binding buffer and eluted with 0.1 M glycine, pH 2.7. Following neutralization with 2 M Tris, mAbs were dialyzed versus PBS.

Characterization of purified anti-LOX-1 monoclonal antibodies by direct ELISA: The figures below shows an example of testing the relative affinities of several anti-LOX-1 mAbs by ELISA (i.e., LOX-1.Ig protein is immobilized on the microtiter plate surface and the antibodies are tested in a dose titration series for their ability to bind to LOX-1.Ig (as detected by an anti-mouse IgG.HRP conjugate reagent). The panels are (left) mAb reactivity to LOX-1.Ig protein; (right) mAb reactivity to hIgGFc protein, and (lower) mAb reactivity to LOX-1.alkaline phosphatase fusion protein. In the latter case, the mAbs are plate bound (through an anti-mouse IgG reagent) and bind a constant amount of LOX-1.AP in solution. Anti-LOX-1 mAbs react specifically to the LOX-1 ectodomain with affinity superior to a commercially procured anti-LOX-1 mAb.

Figure 1:
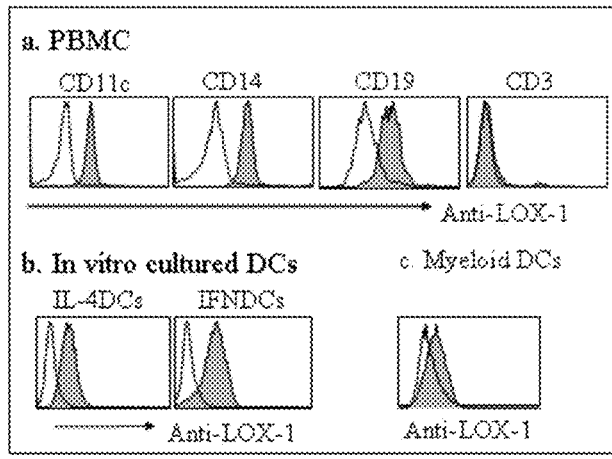
FIGS. 1A, 1B and 1C. Both in vivo and in vitro-cultured DCs express LOX-1.
Figure 1C:
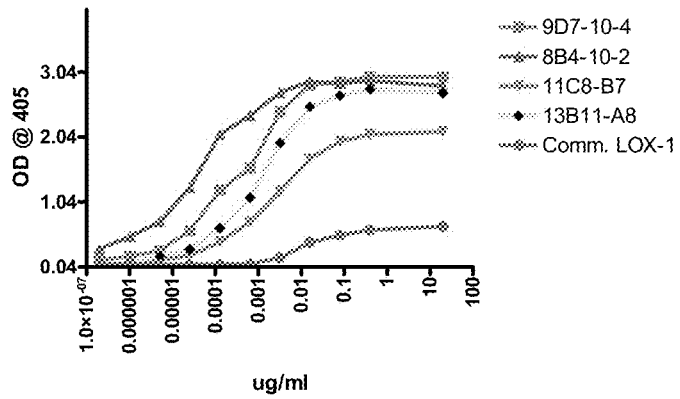

Both in vivo DCs and in vitro-cultured DCs express LOX-1: FIG. 1 shows the expression levels of LOX-1 on PBMCs from normal donors. As shown in FIG. 1a below, antigen presenting cells, including CD11c+DCs, CD14+ monocytes, and CD19+B cells express LOX-1. CD3+ T cells do not express detectable surface LOX-1. Expression levels of LOX-1 on in vitro-cultured DCs and purified blood myeloid (mDCs) are shown in FIG. 1b. Both IL-4 and IFNDCs express significant levels of LOX-1. Although mDCs express high levels of LOX-1, pDCs do not express LOX-1 (not shown), suggesting that manipulating DC through LOX-1 should elicit unique responses since these DC subsets have different functions in vivo.

Figure 2:
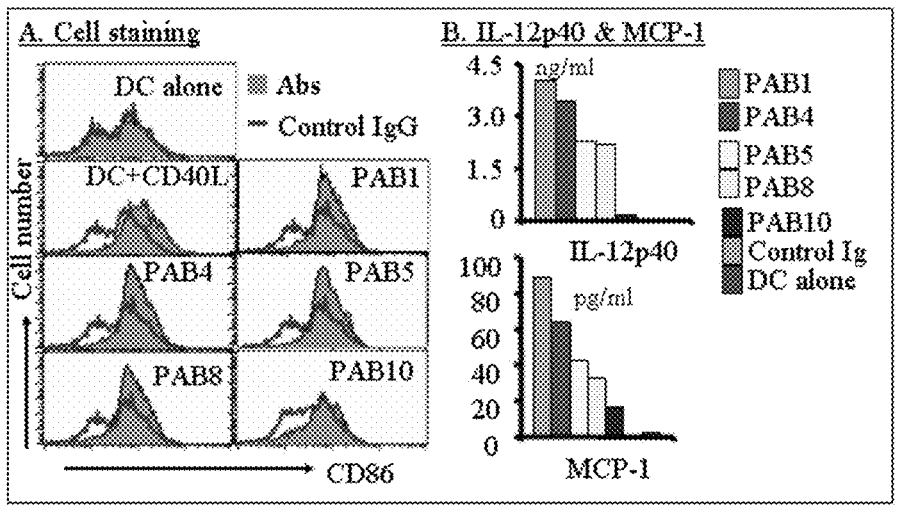
FIGS. 2A and 2B shows that Anti-LOX-1 mAbs activate DCs. IFNDCs were cultured in the plates coated with different clones of mAbs for 18 h.

Signaling through LOX-1 activates DCs and stimulate DCs to produce cytokines and chemokines: Dendritic cells are the primary immune cells that determine the results of immune responses, either induction or tolerance, depending on their activation (19). The role of LOX-1 in DC activation is not known. We generated 8 different clones that produce mouse anti-hLOX-1 mAbs, and we tested whether individual mAbs activate DCs by measuring DC phenotypes and cytokines and chemokines secreted from DCs. Data in FIG. 2A show that PAB1, 4, 5, 8, and 10 could activate DCs, but other anti-LOX-1 mAbs, or control mAbs, did not active DCs (data not shown). In addition, each mAb stimulates DCs to produce different levels of cytokines and chemokines although all mAbs presented in FIG. 2 can induce DC maturation.

Figure 3:
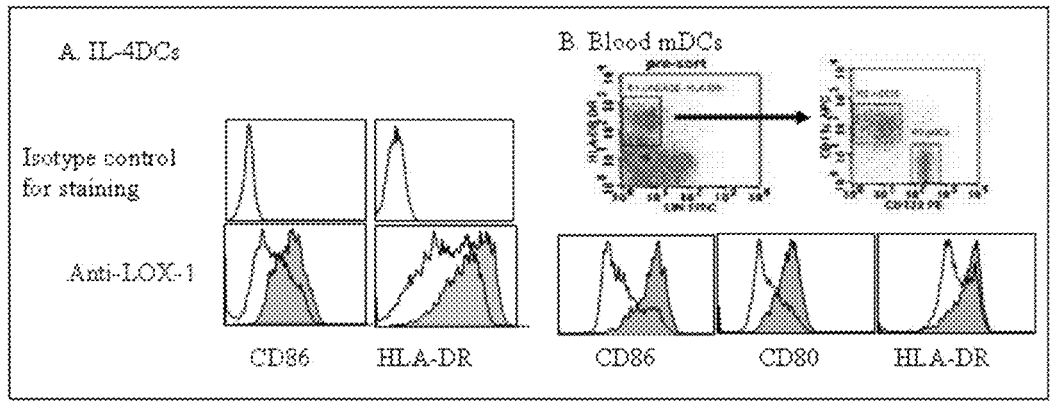
FIGS. 3A and 3B shows that anti-LOX-1 mAbs activate DCs.

FIG. 3 shows that signaling through LOX-1 can result in the activation of DCs. IL-4DCs were stimulated with mAb specific to LOX-1, and data in FIG. 3a show that signals through LOX-1 could activate IL-4DCs, resulting in the increased expression of CD86 and HLA-DR. LOX-1 could also activate IFNDCs (not shown). To test whether LOX-1 can activate in vivo DCs, purified mDCs were stimulated with anti-LOX-1 for 24 h, and then cells were stained with anti-CD86, CD80, and HLA-DR (these are markers of DC activation). As shown in FIG. 3b, LOX-1 can also activate in vivo-derived mDCs to express increased levels of CD86, CD80, and HLA-DR. The latter data are particularly important since they represent the direct biological effects of certain anti-LOX-1 mAbs on ex vivo cells (isolated directly from blood).

Figure 4:
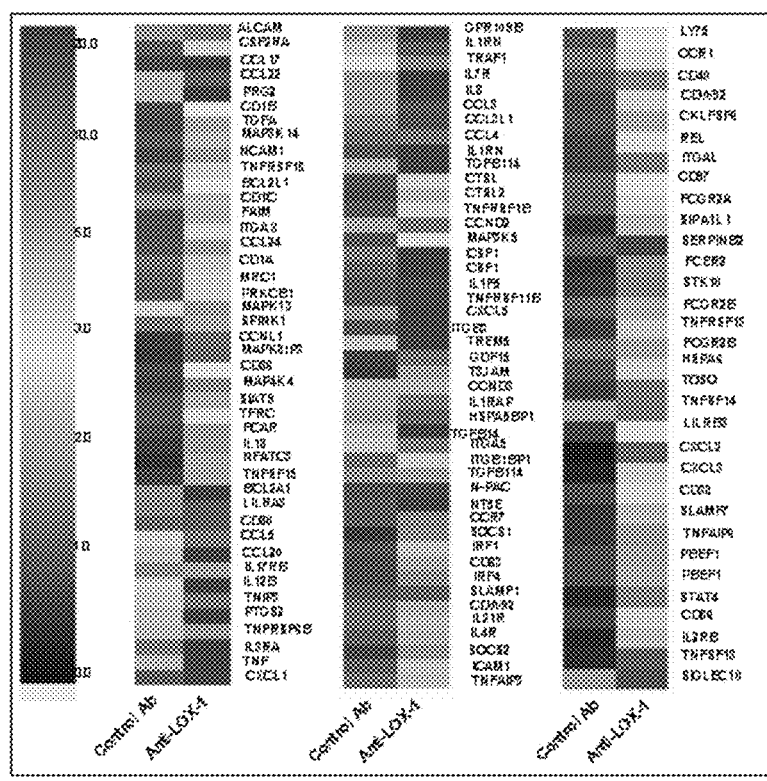
FIG. 4 shows the gene expression profile IL-4DCs were stimulated with either anti-LOX-1 or control mAb for 10 h. Total RNA extracted with RNeasy columns (Qiagen), and analyzed with the 2100 Bioanalyser (Agilent). Biotin-labeled cRNA targets were prepared using the Illumina totalprep labeling kit (Ambion) and hybridized to Sentrix Human6 BeadChips (46K transcripts). These microarrays consist of 50 mer oligonucleotide probes attached to 3 um beads which are lodged into microwells etched at the surface of a silicon wafer. After staining with Streptavidin-Cy3, the array surface was imaged using a sub-micron resolution scanner manufactured by Illumina (Beadstation 500×). A gene expression analysis software program, GeneSpring, Version 7.1 (Agilent), was used to perform data analysis.

Signaling through LOX-1 induce unique activation of DCs: To characterize in more detail DC activation through LOX-1, microarray gene expression analysis was performed. FIG. 4 shows that anti-LOX-1 mAbs stimulate DCs to up- or down-regulate different kinds of genes, showing that signals through LOX-1 result in a unique pattern of DC activation. The data, when compared to signaling through DC-ASGPR and CLEC-6 (not shown), reveal that each cell-surface DC lectin delivers unique signals to activate DCs. Therefore, we expect that DCs activated through different signals will result in different immune responses.

Signaling through LOX-1 activates DCs to secrete cytokines and chemokines: DCs stimulated with LOX-1-specific mAb express increased levels of multiple genes, including co-stimulatory molecules as well as chemokine and cytokine-related genes (FIGS. 5a and b). Both in vitro cultured IL-4DCs and mDCs produced significantly increased amounts of secreted IL-12p40, MCP-1, and IL-8 when they were stimulated with anti-LOX-1 mAb. Increased levels of other cytokines and chemokines including TNFa, IL-6, MIP-1a, and IL-1b, were also observed in the culture supernatants of DCs stimulated with anti-LOX-1. The possible contribution of LLRs in TLR2 and TLR4-mediated immune cell activation has been described previously (14, 20).

Figure 5:
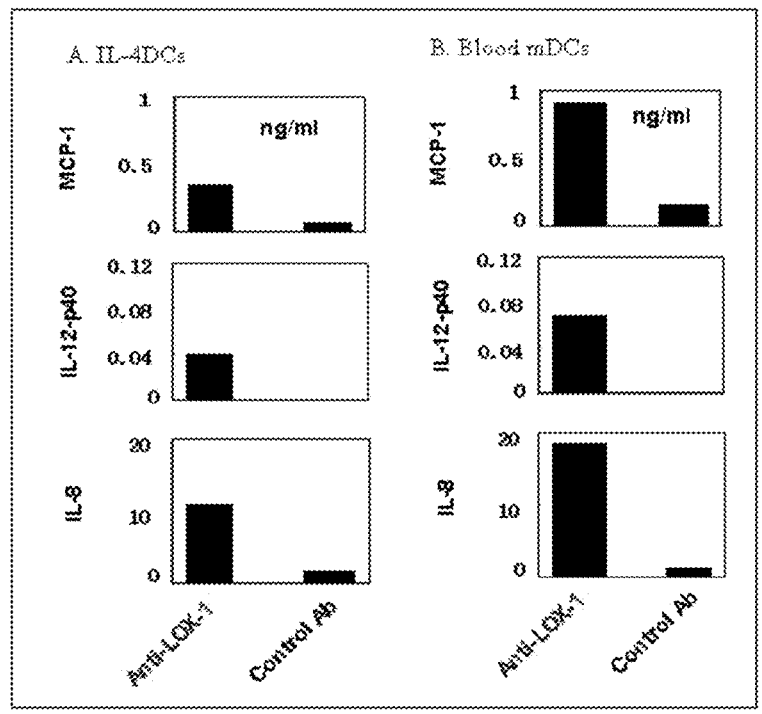
FIGS. 5A and 5B shows that DCs activated with anti-LOX-1 produce increased amounts of cytokines and chemokines. In vitro-cultured IL-4DCs and purified mDCs ($1\times10^5$/200 ul), as described in FIGS. 1A and 1B, respectively, were cultured in the plates coated with anti-LOX-1 mAb (2 ug/well) for 18 h. Culture supernatants were analyzed to measure cytokine and chemokines by Luminex.
Figure 6:
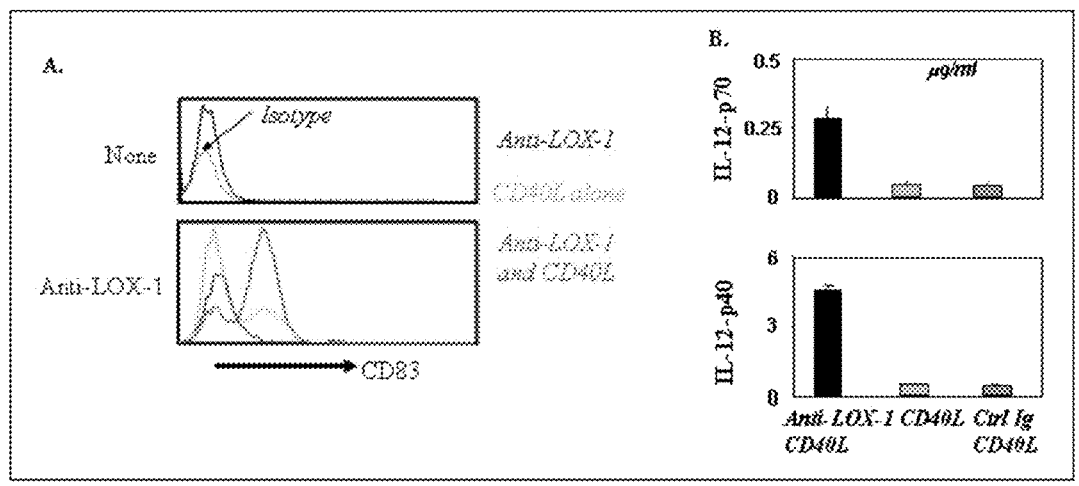
FIGS. 6A and 6B show that the anti-LOX-1 antibody and the CD40 ligand synergize to activate DCs. IL-4DCs ($2\times10^5$/200 ul/well) were cultured in the 96-well plates coated with anti-LOX-1 in the presence or absence of soluble CD40L (20 ng/ml) for 18 h. Control mAbs were also tested. After 18 h, cells were stained with anti-CD83 and culture supernatants were analyzed to measure cytokines and chemokines by Luminex.

Signaling through LOX-1 augments signaling through CD40 DCs: Signals through LOX-1 can synergize with signals through CD40 for enhanced activation of DCs (FIG. 5). LOX-1 engagement during CD40-CD40L interact results in dramatically increased cell surface expression of the activation marker CD83 (FIG. 6a) and increased secretion of IL-12p70 and Il-12p40 (FIG. 6b). This shows that LOX-1 can serve as a co-stimulatory molecule during in vivo DC activation and has broad implications for the therapeutic utility of agents that activate through LOX-1 (either mAbs such as those described here, or natural or surrogate LOX-1 ligands). Taken together, data presented from FIG. 1 to FIG. 6 show that signaling through LOX-1 can activate DCs and that LOX-1 is a novel co-stimulatory molecule for the activation of DCs.

DCs stimulated through LOX-1 induce potent humoral immune responses: -DCs play an important role in humoral immune responses by providing signals for both T-dependent and T-independent B cell responses (21-24) and by transferring antigens to B cells (25, 26). In addition to DCs, signaling through TLR9 as a third signal is necessary for efficient B cell responses (27, 28). LOX-1 can affect DCs-mediated humoral immune responses in the presence of TLR9 ligand, CpG. Six day IL-4 DCs were stimulated with anti-LOX-1 mAb, and then purified B cells were co-cultured. As shown in FIG. 6a, DCs activated with anti-LOX-1 mAb result in remarkably enhanced B cell proliferation (seen via CFSE dilution) and plasma cell differentiation (increase in $CD38^+CD20^-$), compared to DCs stimulated with control mAb. $CD38^+CD20^-$ B cells have a typical morphology of plasma cells, but they do not express CD138. The majority of proliferating cells did not express CCR2, CCR4, CCR6, or CCR7.

Figure 7:
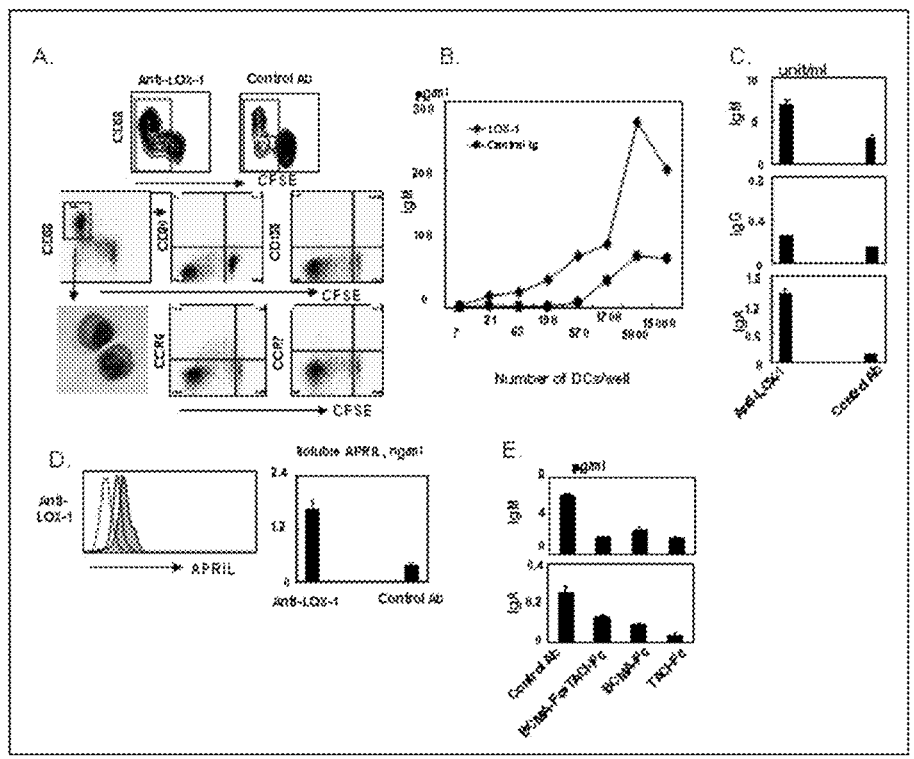
FIGS. 7A to 7E shows that LOX-1 expressed on DCs contributes to enhanced humoral immune responses. Six day GM/IL-4 DCs, $5\times10^3$/well, were incubated in 96 well plates coated with anti-LOX-1 or control mAbs for 16-18 h, and then $1\times10^5$ autologous CD19$^+$ B cells stained with CFSE were co-cultured in the presence of 20 units/ml IL-2 and 50 nM CpG.

The amounts of total immunoglobulins (Igs) produced were measured by ELISA (FIG. 7b). Consistent with the data in FIG. 7a, B cells cultured with anti-LOX-1-stimulated DCs resulted in significantly increased production of total IgM. In addition to the total Ig increase, DCs activated by triggering LOX-1 are more potent than DCs stimulated with control mAb for the production of influenza-virus-specific IgM, IgG, and IgA (FIG. 7c) by B cells, showing that LOX-1-mediated DC activation contributes to both total and antigen specific humoral immune responses.

DC-derived B lymphocyte stimulator protein (BLyS, BAFF) and a proliferation-inducing ligand (APRIL) are important molecules by which DCs can directly regulate human B cell proliferation and function (29-32). Data in FIG. 6d show that DCs stimulated through LOX-1 express increased levels of intracellular APRIL as well as secreted APRIL, but not BLyS (not shown). Expression levels of BLyS and APRIL receptors on B cells in the mixed cultures were measured, but there was no significant change (not shown). This was confirmed by the data in FIG. 7e. During the DC and B cell co-cultures, combinations of BAFF Receptor (BAFFR), TACI and BCMA were blocked with soluble receptor-Fc fusion proteins. Both IgM and IgA productions were significantly decreased when TACI or BCMA was blocked. This was not observed when BAFFR-Fc was added into the cultures, showing that APRIL produced from DCs stimulated with anti-LOX-1 plays an important role in the increased productions of immunoglobulins.

The above discoveries have great implications for the therapeutic application of agents that activate specifically through LOX-1, e.g., as adjuvant in vaccination, or as immune system stimulants for immune compromised individuals. Also, the discovery predicts that blocking natural or abnormally regulated activation via LOX-1 can have applications (e.g., for evoking tolerance in a transplantation setting, or ameliorating autoimmune diseases).

Figure 8:
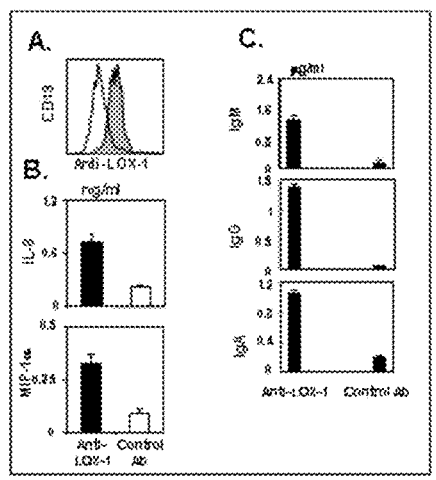
FIGS. 8A to 8C shows that LOX-1 expressed on B cells contributes to B cell activation and immunoglobulin production.

Anti-LOX-1 mAbs activate B cells: CD19+ B cells express LOX-1 (FIG. 1 and FIG. 8a) and this predicts a role for LOX-1 expressed on B cells. Data in FIG. 8b show that triggering LOX-1 on B cells results in the increased production of secreted IL-8 and MIP-1α, suggesting that LOX-1 can directly contribute to B cell activation. In addition to IL-8 and MIP-1α, slight increases in IL-6 and TNFa were also observed when B cells were stimulated with the anti-LOX-1mAb, compared to control mAb. FIG. 8c shows that B cells activated with anti-LOX-1 mAb secret increased amounts of total IgG, IgM, and IgA.

The above discovery of direct effects on B cells through engagement of LOX-1 reinforces the scope of therapeutic application outlined above for agents acting through or against LOX-1.

Figure 9:
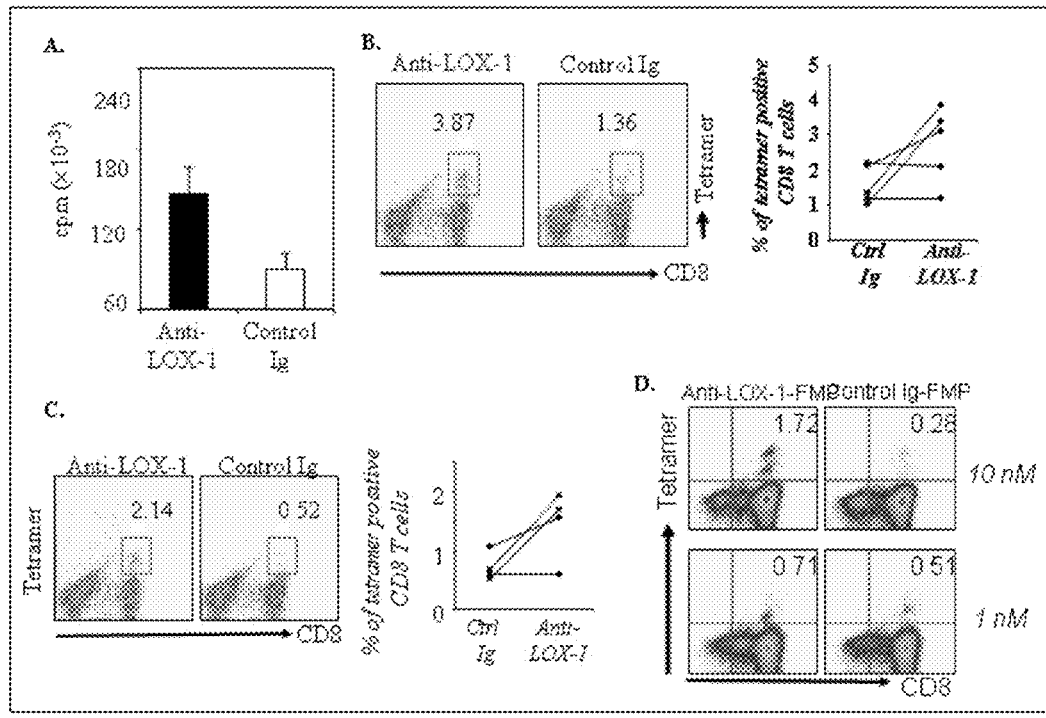
FIGS. 9A to 9D shows that LOX-1 expressed on DCs, contributes to enhanced cellular immune responses.

Role of LOX-1 in T cell responses: DCs stimulated through LOX-1 express enhanced levels of co-stimulatory molecules and produce increased amounts of cytokines and chemokines (FIGS. 1 and 3), suggesting that LOX-1 contributes to cellular immune responses as well as humoral immune responses. This was tested by a mixed lymphocyte reaction (MLR). Proliferation of purified allogeneic T cells was significantly enhanced by DCs stimulated with mAb specific for LOX-1 (FIG. 9a). DCs activated through LOX-1 also prime Mart-1-specific CD8 T cells more efficiently than DC stimulated with control mAb (upper panels in FIG. 9b). More importantly, signaling through LOX-1 permits DCs to cross-prime Mart-1 peptides to CD8 T cells (lower panels in FIG. 9c). Right panels in both FIGS. 9b and 9c show the data generated with cells from 5 and 4 different normal donors, respectively. This indicates that LOX-1 plays an important role in enhancing DC function, resulting in improved priming and cross-priming of antigens to CD8 T cells. Anti-LOX-1 mAb and antigen fusion protein also induce more robust antigen specific CD8 T cell responses than control mAb fusion protein. IL-4DCs were loaded with either 10 or 1 nM of the mAb conjugates with Flu M1 protein, and autologous CD8+ T cells were co-cultured for 7 days. Cells were stained with anti-CD8 and Flu M1 tetramer. Data in FIG. 9d show that anti-LOX-1 fusion protein induced significantly enhanced Flu M1 specific CD8 T cell responses.

It was found that LOX-1 activation of DCs influences neighboring T cells directing them to increase proliferation. Furthermore, when antigen is present during this interaction, LOX-1 activated DCs result in enhance expansion of antigen-specific T cells. This shows that LOX-1 activation, e.g., in a vaccine setting, can direct selective expansion of antigen-specific naïve T cells—this together with the above direct and indirect effects of LOX-1 activation on B cells, clearly predicts the expansion of antigen-specific B cells, and therefore production of antigen-specific antibody. A further demonstration of anti-LOX-1 utility is when antigen is directly focused to DC via an anti-LOX-1 mAb conjugate, the DCs direct the expansion of antigen-specific memory CD8+ cells.

In vivo DCs in non-human primate express LOX-1—To test whether blood DCs in non-human primates (Cynomolgus) are recognized by the anti-human LOX-1 mAbs, monkey PBMC were stained with anti-LOX-1 mAbs and antibodies to other cellular markers, CD3, CD14, CD11c, CD27, CD56, and CD16. Data in FIG. 10 show that both CD14 and CD11c+ cells were stained with anti-human LOX-1 mAbs. Unlike CD14+ and CD11c+ cells, CD3+, CD16+, CD27+, and CD56+ cells did not express LOX-1. This data demonstrates the cross-reactivity of certain anti-human LOX-1 mAbs against monkey antigen presenting cells. This greatly facilitates reducing the inventions described herein to practice, as monkey can be used as a valid model for both efficacy and safely studies of envisioned human therapies.

FIG. 11 shows reduced SDS.PAGE analysis of typical rAb.antigen fusion proteins—including anti-LOX-1_15C4.PSA, which is capable of directing prostate-specific antigen (highlighted grey) to the surface of antigen-presenting cells for the purpose of vaccination against prostate cancer.

Figure 13:
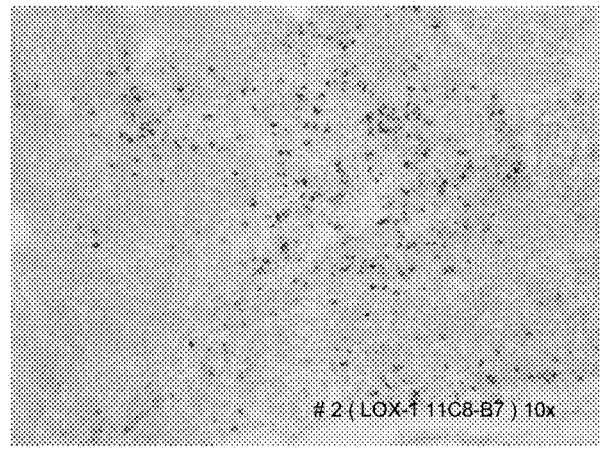

FIGS. 12 and 13 demonstrates directly the ability of an anti-LOX-1 rAb to deliver linked antigen to the surface of LOX-1-bearing cells.

Figure 14:
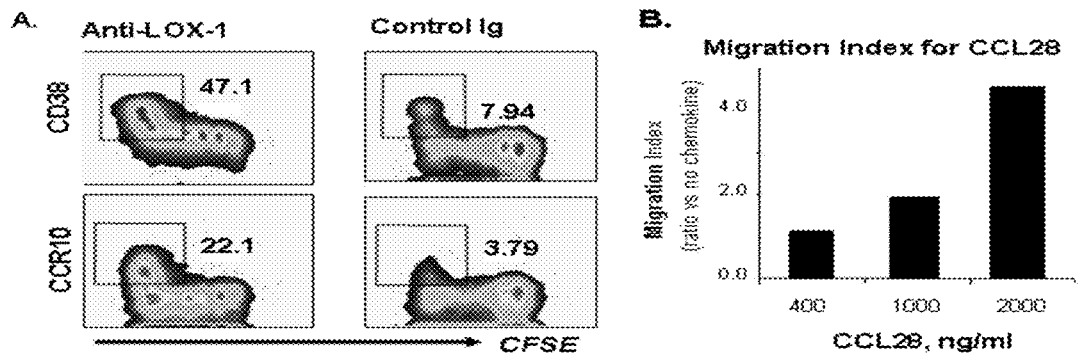

FIGS. 14A and 14B show the mucosal-homing of B cells by DCs activated with anti-LOX-1 mAb. FIG. 14B shows the expression levels of mucosal homolog receptors on B cells were measured. Naïve B cells co-cultured with DCs activated with anti-LOX-1 proliferate better than B cells cultured with DCs stimulated with control immunoglobulin (Ig) (upper two panels in FIG. 14A). With the enhanced proliferation and plasma cell differentiation, naïve B cells co-cultured with DCs stimulated with anti-LOX-1 mAb express CCR10. Those B cells can migrate in response to CCL28. Although CCR10 was known as a distal gut-homing receptor, recent studies show that respiratory mucosa also express significantly amounts of CCL28. Therefore, CCR10 is now demonstrated to be a mucosal-homing receptor.

FIG. 14B shows that B cells interacting with DC activated via LOX-1 are programmed to home to the mucosa. Together with data that shows such DC activate B cell proliferation, differentiation into plasma-like cells, and enhanced secretion of immunoglobulins (including antigen-specific Ig when the LOX-1 activation is associated with antigen targeting via LOX-1) this increased expression of B cell CCR10 demonstrates the high potential of LOX-1 activation and antigen targeting for raising antigen-specific mucosal immunity.

Figure 15:
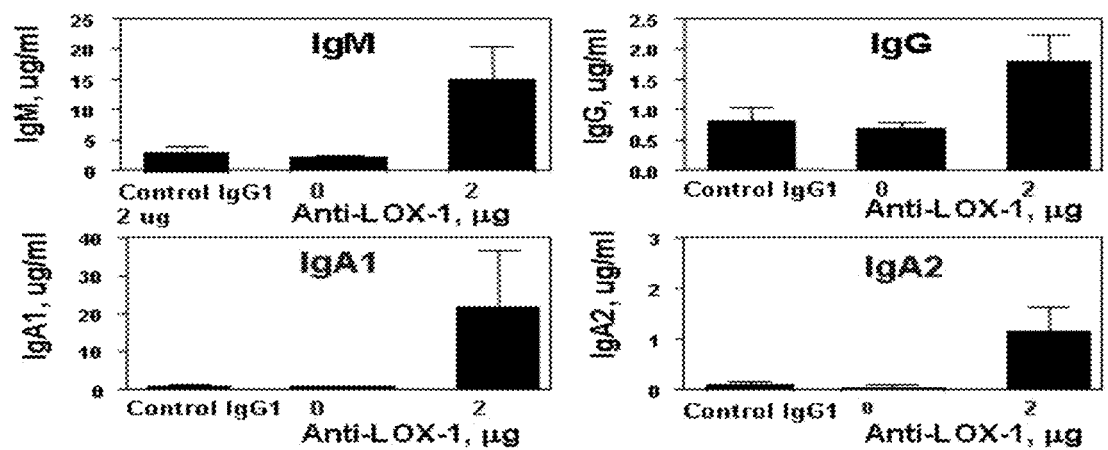

FIG. 15 shows that anti-LOX-1 mAb contribute to the enhanced production of IgA1 and IgA2. Next, whether DCs activated with anti-LOX-1 mAb can induce naïve B cells to produce IgA1 and IgA2 was determined. Naïve B cells (IgD+CD27−) were purified by FACS-sorting. FIG. 15 shows that naïve B cells cultured with DCs activated with anti-LOX-1 result in significantly enhanced IgA1 and IgA2 productions. Both IgM and IgG levels were also enhanced by the DCs stimulated with anti-LOX-1. Taken together, activation of DCs through DC-Lectins, especially LOX-1, may result in enhanced humoral immune responses. In particular, B cells induced with the DCs express mucosal-homing receptor, CCR10, and can produce IgA1 and IgA2. Therefore, vaccines made of anti-LOX-1 will induce potent mucosal immune responses.

Figure 16:
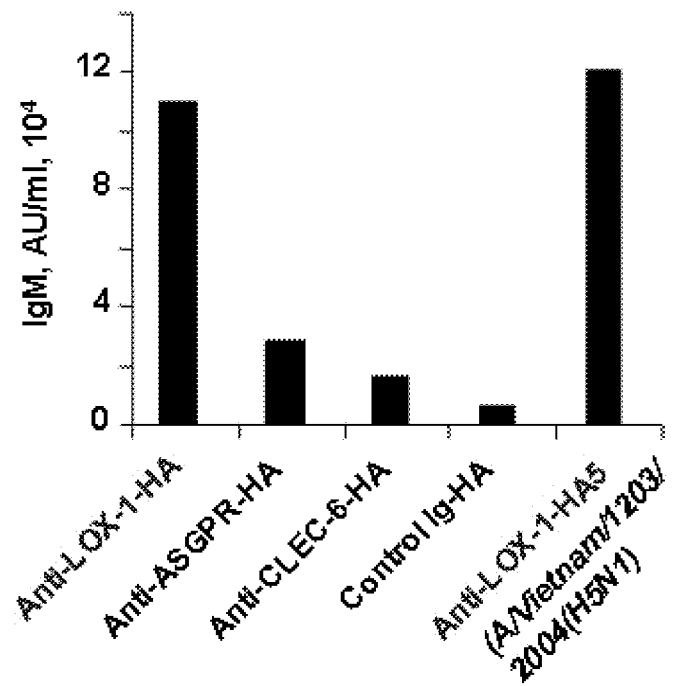

FIG. 16 shows that DCs loaded with recombinant fusion protein of anti-LOX-1 and influenza viral hemagglutinin (HA1, H1N1, PR8) induce naïve B cells to secrete flu-specific IgM. Compared to anti-LOX-1, HA1 fusion proteins of both anti-ASGPR and anti-CLEC-6 resulted in weak responses. Naïve B cells co-cultured with the DCs loaded with anti-LOX-1-HA5 also produced HA1-specific IgM. Taken together, vaccines made of anti-Lectin mAbs and antigens may induce potent mucosal IgA1 and IgA2 responses that prevent viral infections.

Figure 17:
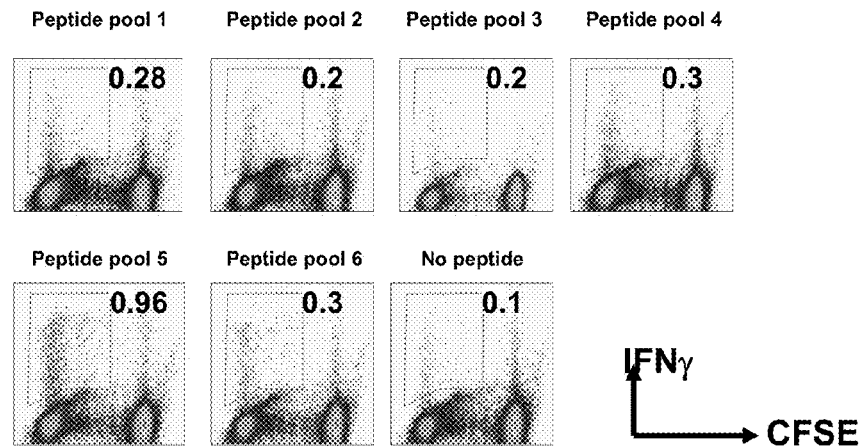

FIG. 17 shows that anti-LOX-1-HA5 targeted DCs also have the capacity to expand HA5-specific CD4+ T cells, further demonstrating the utility of the present invention as a potent vaccine.

Figure 18:
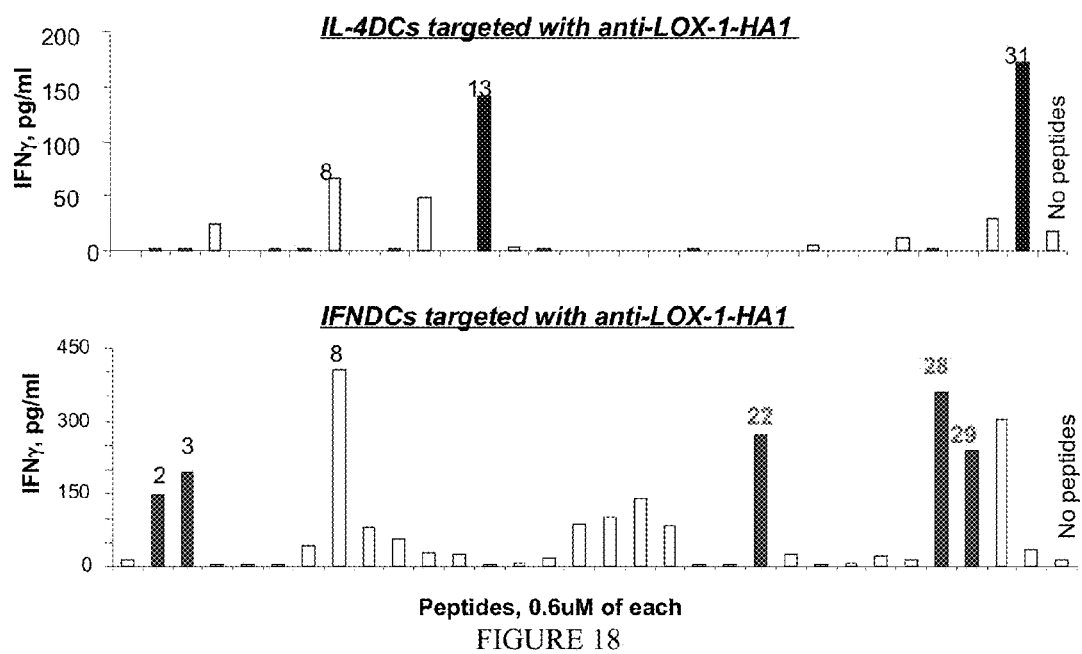

FIG. 18 shows that an anti-LOX-1 vaccine elicits DC-subset-specific immune responses. Whether different DC subsets targeted with anti-LOX-1-HA5 vaccine elicit a different range of immune responses as demonstrated by expansion of HA5-specific T cells as defined by their stimulation with HA5 peptides was determined. Thus, anti-LOX-1-based vaccines, by targeting the same antigen to different DC subtypes result in a broad immune responses directed against the antigen. These data also highlight the desired property of anti-LOX-1 targeting vaccine in eliciting antigen specific T cell responses that are highly predicted to be effector cells as characterized by their production of IFNγ.

Figure 19:
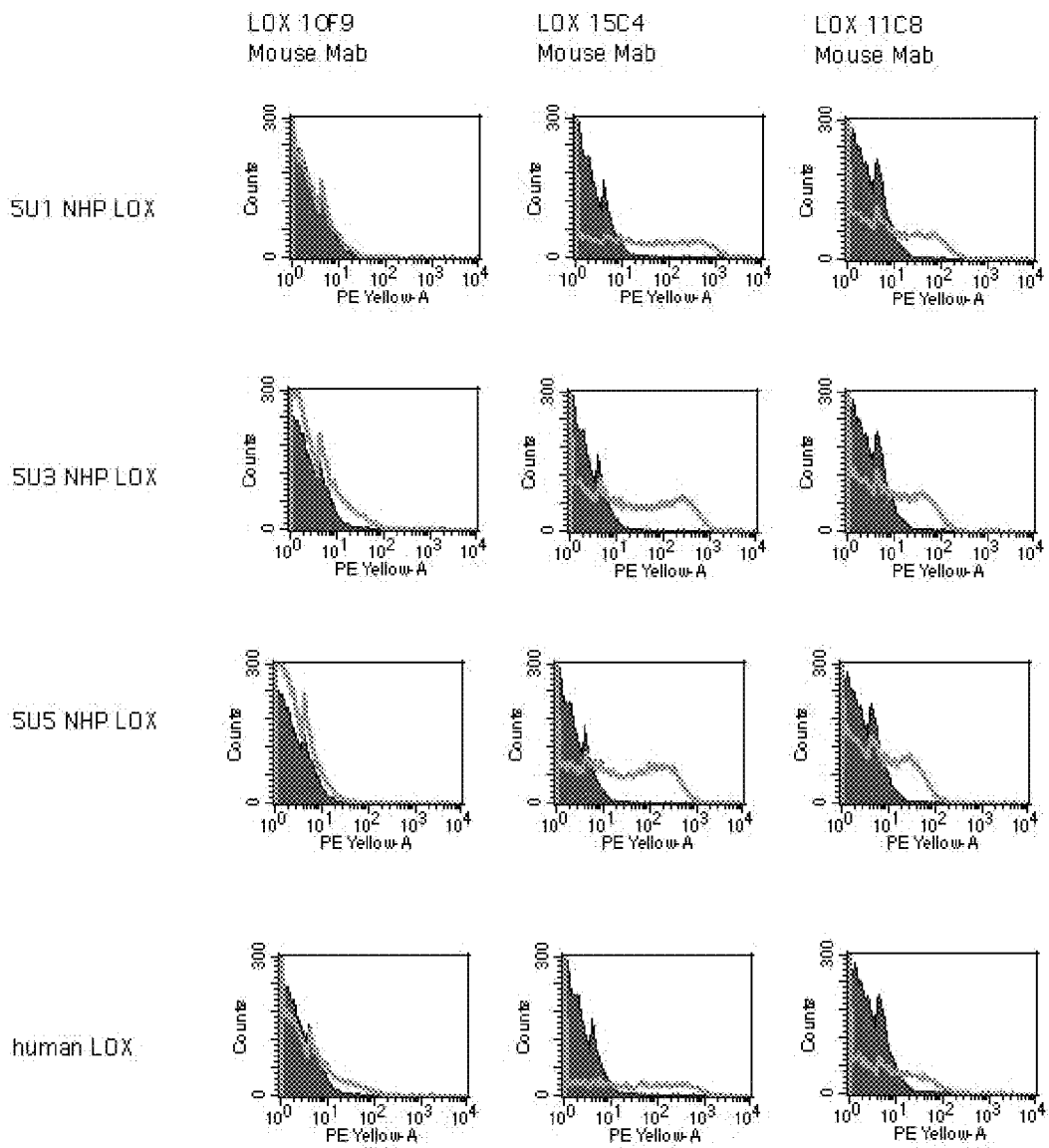

FIG. 19 shows the cross-reactivity of anti-LOX-1 antibodies to macaque LOX-1. cDNA clones corresponding to 4 variant LOX-1 cDNAs were isolated from macaque and configured them in a mammalian expression vector. FIG. 19 shows a FACS analysis of three particularly desirable anti-human LOX-1 antibodies on 293F cells transfected with these expression vectors versus 293F cells transfected with a human LOX-1 expression vector. The results show that all two of the mAbs tested (15C4 and 11C8) cross-react to all three macaque LOX-1 variants tested, while 10F9 cross-reacted to one of the variants. Such cross reactivity is desirable since it permits mechanism-based toxicity and efficacy testing in NHP models prior to human clinical trials.

FIG. 20 shows a Clustal W alignment of the four variants of sequences from macaques (5UI-5U4) with human LOX-1.

FIG. 21A to 21D show that antigens delivered through LOX-1 result in antigen specific CD4 T cell responses. Binding affinity of anti-LOX-1-HA1 and control IG-HA1 was tested (FIG. 21A). Both anti-LOX-1-HA1 and control Ig-HA1 can bind to monocyte-derived IFNDCs, but anti-LOX- 1-HA1 binds slightly better than control Ig-HA1 to the DCs. CD4 T cell proliferation induced by DCs loaded with anti-LOX-1-HA1 or control Ig-HA1 was measured. FIG. 21B shows that IFNDCs loaded with anti-LOX-1-HA1 induced greater CD4 T cell proliferation (69%) than control Ig-HA1 did (7%).

To determine whether the proliferating CD4 T cells are antigen (HA1)-specific or not, CD4 T cells expanded with DC loaded with anti-LOX-1-HA1 were restimulated with IFNDCs loaded with peptide pools of HA1. FIG. 21C shows that peptide pool 37-48 resulted in relatively higher frequency of IFNγ-producing CD4 T cells. The responsiveness of CD4 T cells to individual peptides in peptide pool 37-48 was also determined. FIG. 21D shows that CD4 T cells produce intracellular IFNγ in response to three peptides, peptide43, peptide 44, and peptide 45. Taken together, these data demonstrate that targeting human DCs with anti-LOX-1-HA1 can induce antigen specific CD4 T cell responses.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Delneste, Y., G. Magistrelli, J. Gauchat, J. Haeuw, J. Aubry, K. Nakamura, N. Kawakami-Honda, L. Goetsch, T. Sawamura, J. Bonnefoy, and P. Jeannin. 2002. Involvement of LOX-1 in dendritic cell-mediated antigen cross-presentation. Immunity 17:353-362.
2. Figdor, C. G., Y. van Kooyk, and G. J. Adema. 2002. C-type lectin receptors on dendritic cells and Langerhans cells. Nat Rev Immunol 2:77-84.
3. Pyz, E., A. S. Marshall, S. Gordon, and G. D. Brown. 2006. C-type lectin-like receptors on myeloid cells. Ann Med 38:242-251.
4. Brown, G. D. 2006. Dectin-1: a signalling non-TLR pattern-recognition receptor. Nat Rev Immunol 6:33-43.
5. Geijtenbeek, T. B., D. J. Krooshoop, D. A. Bleijs, S. J. van Vliet, G. C. van Duijnhoven, V. Grabovsky, R. Alon, C. G. Figdor, and Y. van Kooyk. 2000. DC-SIGN-ICAM-2 interaction mediates dendritic cell trafficking. Nat Immunol 1:353-357.
6. Geijtenbeek, T. B., R. Torensma, S. J. van Vliet, G. C. van Duijnhoven, G. J. Adema, Y. van Kooyk, and C. G. Figdor. 2000. Identification of DC-SIGN, a novel dendritic cell-specific ICAM-3 receptor that supports primary immune responses. Cell 100:575-585.
7. d'Ostiani, C. F., G. Del Sero, A. Bacci, C. Montagnoli, A. Spreca, A. Mencacci, P. Ricciardi-Castagnoli, and L. Romani. 2000. Dendritic cells discriminate between yeasts and hyphae of the fungus Candida albicans. Implications for initiation of T helper cell immunity in vitro and in vivo. J Exp Med 191:1661-1674.
8. Fradin, C., D. Poulain, and T. Jouault. 2000. beta-1,2-linked oligomannosides from Candida albicans bind to a 32-kilodalton macrophage membrane protein homologous to the mammalian lectin galectin-3. Infect Immun 68:4391-4398.
9. Cambi, A., K. Gijzen, J. M. de Vries, R. Torensma, B. Joosten, G. J. Adema, M. G. Netea, B. J. Kullberg, L. Romani, and C. G. Figdor. 2003. The C-type lectin DC-SIGN (CD209) is an antigen-uptake receptor for Candida albicans on dendritic cells. Eur J Immunol 33:532-538.
10. Netea, M. G., J. W. Meer, I. Verschueren, and B. J. Kullberg. 2002. CD40/CD40 ligand interactions in the host defense against disseminated Candida albicans infection: the role of macrophage-derived nitric oxide. Eur J Immunol 32:1455-1463.

11. Lee, S. J., S. Evers, D. Roeder, A. F. Parlow, J. Risteli, L. Risteli, Y. C. Lee, T. Feizi, H. Langen, and M. C. Nussenzweig. 2002. Mannose receptor-mediated regulation of serum glycoprotein homeostasis. Science 295:1898-1901.
12. Maeda, N., J. Nigou, J. L. Herrmann, M. Jackson, A. Amara, P. H. Lagrange, G. Puzo, B. Gicquel, and O, Neyrolles. 2003. The cell surface receptor DC-SIGN discriminates between *Mycobacterium* species through selective recognition of the mannose caps on lipoarabinomannan. J Biol Chem 278:5513-5516.
13. Tailleux, L., O, Schwartz, J. L. Herrmann, E. Pivert, M. Jackson, A. Amara, L. Legres, D. Dreher, L. P. Nicod, J. C. Gluckman, P. H. Lagrange, B. Gicquel, and O, Neyrolles. 2003. DC-SIGN is the major *Mycobacterium tuberculosis* receptor on human dendritic cells. J Exp Med 197:121-127.
14. Geijtenbeek, T. B., S. J. Van Vliet, E. A. Koppel, M. Sanchez-Hernandez, C. M. Vandenbroucke-Grauls, B. Appelmelk, and Y. Van Kooyk. 2003. *Mycobacteria* target DC-SIGN to suppress dendritic cell function. J Exp Med 197:7-17.
15. Cooper, A. M., A. Kipnis, J. Turner, J. Magram, J. Ferrante, and I. M. Orme. 2002. Mice lacking bioactive IL-12 can generate protective, antigen-specific cellular responses to mycobacterial infection only if the IL-12 p40 subunit is present. J Immunol 168:1322-1327.
16. Bates, E. E., N. Fournier, E. Garcia, J. Valladeau, I. Durand, J. J. Pin, S. M. Zurawski, S. Patel, J. S. Abrams, S. Lebecque, P. Garrone, and S. Saeland. 1999. APCs express DCIR, a novel C-type lectin surface receptor containing an immunoreceptor tyrosine-based inhibitory motif. J Immunol 163:1973-1983.
17. Bendtsen, J. D., H. Nielsen, G. von Heijne, and S. Brunak. 2004. Improved prediction of signal peptides: SignalP 3.0. J Mol Biol 340:783-795.
18. Shulman, M., C. D. Wilde, G. Kohler, M. J. Shulman, N. S. Rees, D. Atefi, J. T. Horney, S. B. Eaton, W. Whaley, J. T. Galambos, H. Hengartner, L. R. Shapiro, and L. Zemek. 1978.
19. Banchereau, J., F. Briere, C. Caux, J. Davoust, S. Lebecque, Y. J. Liu, B. Pulendran, and K. Palucka. 2000. Immunobiology of dendritic cells. Annu Rev Immunol 18:767-811.
20. Jeannin, P., B. Bottazzi, M. Sironi, A. Doni, M. Rusnati, M. Presta, V. Maina, G. Magistrelli, J. F. Haeuw, G. Hoeffel, N. Thieblemont, N. Corvaia, C. Garlanda, Y. Delneste, and A. Mantovani. 2005. Complexity and complementarity of outer membrane protein A recognition by cellular and humoral innate immunity receptors. Immunity 22:551-560.
21. Wykes, M., and G. MacPherson. 2000. Dendritic cell-B-cell interaction: dendritic cells provide B cells with CD40-independent proliferation signals and CD40-dependent survival signals. Immunology 100:1-3.
22. Balazs, M., F. Martin, T. Zhou, and J. Kearney. 2002. Blood dendritic cells interact with splenic marginal zone B cells to initiate T-independent immune responses. Immunity 17:341-352.
23. Kikuchi, T., S. Worgall, R. Singh, M. A. Moore, and R. G. Crystal. 2000. Dendritic cells genetically modified to express CD40 ligand and pulsed with antigen can initiate antigen-specific humoral immunity independent of CD4+ T cells. Nat Med 6:1154-1159.
24. Dubois, B., J. M. Bridon, J. Fayette, C. Barthelemy, J. Banchereau, C. Caux, and F. Briere. 1999. Dendritic cells directly modulate B cell growth and differentiation. J Leukoc Biol 66:224-230.
25. Qi, H., J. G. Egen, A. Y. Huang, and R. N. Germain. 2006. Extrafollicular activation of lymph node B cells by antigen-bearing dendritic cells. Science 312:1672-1676.
26. Bergtold, A., D. D. Desai, A. Gavhane, and R. Clynes. 2005. Cell surface recycling of internalized antigen permits dendritic cell priming of B cells. Immunity 23:503-514.
27. Ruprecht, C. R., and A. Lanzavecchia. 2006. Toll-like receptor stimulation as a third signal required for activation of human naive B cells. Eur J Immunol 36:810-816.
28. Bernasconi, N. L., E. Traggiai, and A. Lanzavecchia. 2002. Maintenance of serological memory by polyclonal activation of human memory B cells. Science 298:2199-2202.
29. Moore, P. A., O. Belvedere, A. Orr, K. Pieri, D. W. LaFleur, P. Feng, D. Soppet, M. Charters, R. Gentz, D. Parmelee, Y. Li, O. Galperina, J. Giri, V. Roschke, B. Nardelli, J. Carrell, S. Sosnovtseva, W. Greenfield, S. M. Ruben, H. S. Olsen, J. Fikes, and D. M. Hilbert. 1999. BLyS: member of the tumor necrosis factor family and B lymphocyte stimulator. Science 285:260-263.
30. Gross, J. A., J. Johnston, S. Mudri, R. Enselman, S. R. Dillon, K. Madden, W. Xu, J. Parrish-Novak, D. Foster, C. Lofton-Day, M. Moore, A. Littau, A. Grossman, H. Haugen, K. Foley, H. Blumberg, K. Harrison, W. Kindsvogel, and C. H. Clegg. 2000. TACI and BCMA are receptors for a TNF homologue implicated in B-cell autoimmune disease. Nature 404:995-999.
31. Craxton, A., D. Magaletti, E. J. Ryan, and E. A. Clark. 2003. Macrophage- and dendritic cell—dependent regulation of human B-cell proliferation requires the TNF family ligand BAFF. Blood 101:4464-4471.
32. MacLennan, I., and C. Vinuesa. 2002. Dendritic cells, BAFF, and APRIL: innate players in adaptive antibody responses. Immunity 17:235-238.

What is claimed is:

1. A method for increasing the effectiveness of antigen presentation by a LOX-1-expressing antigen presenting cell comprising the steps of:
providing a human antigen presenting cell;
contacting the antigen presenting cell with an anti-human LOX-1-specific antibody capable of increasing antigen presentation by the antigen presenting cell, wherein the antigen presenting cell is activated;
activating in vitro the antigen presenting cell with GM-CSF and IL-4 or Interferon alpha; and
increasing the surface expression of CD86 and HLA-DR on the antigen presenting cell through the contact with the LOX-1-specific antibody.

2. The method of claim 1, wherein the antigen presenting cell comprises an isolated dendritic cell, a peripheral blood mononuclear cell, a monocyte, a myeloid dendritic cell and combinations thereof.

3. The method of claim 1, wherein the antigen presenting cell comprises an isolated dendritic cell, a peripheral blood mononuclear cell, a monocyte, a B cell, a myeloid dendritic cell and combinations thereof that have been cultured in vitro with interferon alpha, an antigen or a combinations thereof.

4. The method of claim 1, wherein the antigen presenting cell comprises a human dendritic cell that has been contacted with Interferon alpha to activate the dendritic cell, wherein the activated dendritic cell increases the surface expression of CD80.

5. The method of claim 1, wherein the antigen presenting cell comprises a dendritic cell and the activated dendritic cell increases the secretion of IL-12p40, MCP-1, IL-8, TNFa, IL-6, MIP-1a, and IL-1b.

6. The method of claim 1, wherein the antigen presenting cell comprises a dendritic cell and increases the activation in conjunction with signaling through CD40.

7. The method of claim 1, wherein the antigen presenting cell comprises a dendritic cell having an increase in co-stimulatory activity.

8. The method of claim 1, wherein the human antigen presenting cell comprises a dendritic cell contacted with the LOX-1-specific antibody or fragment thereof have a change in expression profile in one or more genes selected from ALCAM; CSF2RA; CCL17; CCL22; PRG2; CD1B; TGFA; MAPSK14; NCAM1; TNFRSF18; BCL2L1; CD1C; FAIM; ITGAX; CCL24; CD1A; MRC1; PRKCB1; MAPK13; SPINK1; CCNL1; MAPK8IPS; CDGG; MAP4K4; SLATS; TFRC; IL18; NFATCS; TNFSF15; BCL2A1; LILRAS; CDG0; CCL5; CCL20; IL17RB; IL12B; TNIPS; PTGS2; TNFRSPGS; ILSRA; TNF; and CXCL1.

* * * * *

UNITED STATES PATENT AND TRADEMARK OFFICE
CERTIFICATE OF CORRECTION

PATENT NO. : 8,481,314 B2
APPLICATION NO. : 12/036138
DATED : July 9, 2013
INVENTOR(S) : Jacques F. Banchereau et al.

It is certified that error appears in the above-identified patent and that said Letters Patent is hereby corrected as shown below:

In the Claims

Claim 1, column 65, line 45, delete "a human antigen presenting cell" and insert -- an isolated LOX-1 expressing human antigen presenting cell -- therefor.

Claim 1, column 65, lines 47-54, delete "antibody capable of increasing antigen presentation by the antigen presenting cell, wherein the antigen presenting cell is activated; activating in vitro the antigen presenting cell with GM-CSF and IL-4 or Interferon alpha; and increasing the surface expression of CD86 and HLA-DR on the antigen presenting cell through the contact with the LOX-1-specific antibody." and insert -- antibody in vitro, wherein the antibody is capable of increasing the surface expression of CD86 and HLA-DR on the antigen presenting cell, activating the antigen presenting cell, and increasing antigen presentation by the antigen presenting cell. -- therefor.

Claim 2, column 65, lines 56-57, delete "peripheral blood mononuclear" and insert -- B -- therefor.

Claim 3, column 65, lines 60-63, delete "comprises an isolated dendritic cell, a peripheral blood mononuclear cell, a monocyte, a B cell, a myeloid dendritic cell and combinations therefore that have been cultured in vitro with interferon alpha" and insert -- has been further cultured in vitro with GM-CSF and IL-4, interferon-alpha, an antigen, or a combination thereof -- therefor.

Claim 8, column 66, line 55, delete "contacted" and insert -- and the contact -- therefor.

Claim 8, column 66, line 56, delete "or fragment thereof have" and insert -- results in -- therefor.

Signed and Sealed this
Fifteenth Day of October, 2013

Teresa Stanek Rea
*Deputy Director of the United States Patent and Trademark Office*

UNITED STATES PATENT AND TRADEMARK OFFICE
CERTIFICATE OF CORRECTION

PATENT NO. : 8,481,314 B2
APPLICATION NO. : 12/036138
DATED : July 9, 2013
INVENTOR(S) : Banchereau et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1205 days.

Signed and Sealed this
Thirtieth Day of December, 2014

Michelle K. Lee
*Deputy Director of the United States Patent and Trademark Office*

SEQUENCE LISTING

```
<160> NUMBER OF SEQ ID NOS: 24

<210> SEQ ID NO 1
<211> LENGTH: 186
<212> TYPE: DNA
<213> ORGANISM: Artificial
<220> FEATURE:
<223> OTHER INFORMATION: Chemically Synthesized Oligonucleotide

<400> SEQUENCE: 1
gacaccaccg aggcccgcca cccccacccc cccgtgacca cccccaccac caccgaccgg    60
```

```
aagggcacca ccgccgagga gctggccggc atcggcatcc tgaccgtgat cctgggcggc    120
aagcggacca acaacagcac ccccaccaag ggcgaattct gcagatatcc atcacactgg    180
cggccg                                                                186
```

```
<210> SEQ ID NO 2
<211> LENGTH: 61
<212> TYPE: PRT
<213> ORGANISM: Artificial
<220> FEATURE:
<223> OTHER INFORMATION: Chemically Synthesized Polypeptide

<400> SEQUENCE: 2

Asp Thr Thr Glu Ala Arg His Pro His Pro Val Thr Thr Pro Thr
1               5                  10                  15

Thr Asp Arg Lys Gly Thr Thr Ala Glu Glu Leu Ala Gly Ile Gly Ile
            20                  25                  30

Leu Thr Val Ile Leu Gly Gly Lys Arg Thr Asn Asn Ser Thr Pro Thr
        35                  40                  45

Lys Gly Glu Phe Cys Arg Tyr Pro Ser His Trp Arg Pro
    50                  55                  60
```

```
<210> SEQ ID NO 3
<211> LENGTH: 444
<212> TYPE: PRT
<213> ORGANISM: Artificial
<220> FEATURE:
<223> OTHER INFORMATION: Chemically Synthesized Polypeptide

<400> SEQUENCE: 3

Glu Val Gln Leu Gln Gln Ser Gly Thr Val Leu Ala Arg Pro Gly Ala
1               5                  10                  15

Ser Val Lys Met Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Ala Ile Tyr Pro Gly Asn Ser Asp Thr Thr Tyr Asn Gln Lys Phe
    50                  55                  60

Lys Gly Lys Ala Lys Leu Thr Ala Val Thr Ser Thr Ser Thr Ala Tyr
65                  70                  75                  80

Met Glu Leu Ser Ser Leu Thr Asn Glu Asp Ser Ala Val Tyr Tyr Cys
                85                  90                  95

Thr Pro Thr Tyr Tyr Phe Asp Tyr Trp Gly Gln Gly Thr Ser Leu Thr
            100                 105                 110

Val Ser Ser Ala Lys Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
    210                 215                 220
```

```
Pro Ala Pro Glu Phe Glu Gly Gly Pro Ser Val Phe Leu Phe Pro Pro
225                 230                 235                 240

Lys Pro Lys Asp Thr Leu Met Ile Ser Arg Thr Pro Glu Val Thr Cys
            245                 250                 255

Val Val Val Asp Val Ser Gln Glu Asp Pro Glu Val Gln Phe Asn Trp
                260                 265                 270

Tyr Val Asp Gly Val Glu Val His Asn Ala Lys Thr Lys Pro Arg Glu
            275                 280                 285

Glu Gln Phe Asn Ser Thr Tyr Arg Val Val Ser Val Leu Thr Val Leu
        290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly Lys Ala Ser
        435                 440

<210> SEQ ID NO 4
<211> LENGTH: 219
<212> TYPE: PRT
<213> ORGANISM: Artificial
<220> FEATURE:
<223> OTHER INFORMATION: Chemically Synthesized Polypeptide

<400> SEQUENCE: 4

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Phe Leu Gln Arg Pro Gly Gln Ser
        35                  40                  45

Pro Lys Arg Leu Ile Tyr Leu Val Ser Lys Leu Asp Ser Gly Val Pro
50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Trp Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140
```

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 5
<211> LENGTH: 442
<212> TYPE: PRT
<213> ORGANISM: Artificial
<220> FEATURE:
<223> OTHER INFORMATION: Chemically Synthesized Polypeptide

<400> SEQUENCE: 5

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Gly Ser Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Asn Thr Asn Tyr Asn Glu Asn Phe
    50                  55                  60

Lys Gly Lys Ala Thr Phe Thr Ala Asp Thr Ser Ser Asn Thr Ala Tyr
65                  70                  75                  80

Met Gln Leu Thr Ser Leu Thr Ser Glu Asp Ser Ala Val Tyr Tyr Cys
                85                  90                  95

Ala Arg Ala Gly Ile Tyr Trp Gly Gln Gly Thr Leu Val Thr Val Ser
            100                 105                 110

Ala Ala Lys Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Glu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln

```
                    290                 295                 300
Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys Ala Ser
        435                 440
```

<210> SEQ ID NO 6
<211> LENGTH: 218
<212> TYPE: PRT
<213> ORGANISM: Artificial
<220> FEATURE:
<223> OTHER INFORMATION: Chemically Synthesized Polypeptide

<400> SEQUENCE: 6

```
Asp Ile Val Leu Thr Gln Ser Pro Ala Phe Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Val Ala Ser Lys Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Arg Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

-continued

<210> SEQ ID NO 7
<211> LENGTH: 449
<212> TYPE: PRT
<213> ORGANISM: Artificial
<220> FEATURE:
<223> OTHER INFORMATION: Chemically Synthesized Polypeptide

<400> SEQUENCE: 7

```
Glu Ile Gln Leu Gln Gln Thr Gly Pro Glu Leu Val Lys Pro Gly Ala
1               5                   10                  15

Ser Val Lys Ile Ser Cys Lys Ala Ser Gly Tyr Pro Phe Thr Asp Tyr
            20                  25                  30

Ile Met Val Trp Val Lys Gln Ser His Gly Lys Ser Leu Glu Trp Ile
        35                  40                  45

Gly Asn Ile Ser Pro Tyr Tyr Gly Thr Thr Asn Tyr Asn Leu Lys Phe
    50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Ser Pro Asn Trp Asp Gly Ala Trp Phe Ala His Trp Gly Gln
            100                 105                 110

Gly Ala Leu Val Thr Val Ser Ala Ala Lys Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365
```

```
Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys Ala
            435                 440                 445

Ser

<210> SEQ ID NO 8
<211> LENGTH: 218
<212> TYPE: PRT
<213> ORGANISM: Artificial
<220> FEATURE:
<223> OTHER INFORMATION: Chemically Synthesized Polypeptide

<400> SEQUENCE: 8

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Phe Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Phe Thr Phe Gly Ser Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 9
<211> LENGTH: 783
<212> TYPE: PRT
<213> ORGANISM: Artificial
<220> FEATURE:
<223> OTHER INFORMATION: Chemically Synthesized Polypeptide

<400> SEQUENCE: 9

Glu Ile Gln Leu Gln Gln Thr Gly Pro Glu Leu Val Lys Pro Gly Ala
```

-continued

```
1               5                   10                  15
Ser Val Lys Ile Ser Cys Lys Ala Ser Gly Tyr Pro Phe Thr Asp Tyr
                20                  25                  30

Ile Met Val Trp Val Lys Gln Ser His Gly Lys Ser Leu Glu Trp Ile
                35                  40                  45

Gly Asn Ile Ser Pro Tyr Tyr Gly Thr Thr Asn Tyr Asn Leu Lys Phe
            50                  55                  60

Lys Gly Lys Ala Thr Leu Thr Val Asp Lys Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Ser Pro Asn Trp Asp Gly Ala Trp Phe Ala His Trp Gly Gln
                100                 105                 110

Gly Ala Leu Val Thr Val Ser Ala Ala Lys Thr Lys Gly Pro Ser Val
                115                 120                 125

Phe Pro Leu Ala Pro Cys Ser Arg Ser Thr Ser Glu Ser Thr Ala Ala
                130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
                195                 200                 205

Pro Ser Asn Thr Lys Val Asp Lys Arg Val Glu Ser Lys Tyr Gly Pro
                210                 215                 220

Pro Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
                275                 280                 285

Thr Lys Pro Arg Glu Glu Gln Phe Asn Ser Thr Tyr Arg Val Val Ser
                290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
                370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430
```

His Asn His Tyr Thr Gln Lys Ser Leu Ser Leu Ser Leu Gly Lys Ala
            435                 440                 445

Ser Asp Thr Thr Glu Pro Ala Thr Pro Thr Thr Pro Val Thr Thr Asp
450                 455                 460

Gln Ile Cys Ile Gly Tyr His Ala Asn Ser Thr Glu Gln Val Asp
465                 470                 475                 480

Thr Ile Met Glu Lys Asn Val Thr Val Thr His Ala Gln Asp Ile Leu
                485                 490                 495

Glu Lys Lys His Asn Gly Lys Leu Cys Asp Leu Asp Gly Val Lys Pro
            500                 505                 510

Leu Ile Leu Arg Asp Cys Ser Val Ala Gly Trp Leu Leu Gly Asn Pro
        515                 520                 525

Met Cys Asp Glu Phe Ile Asn Val Pro Glu Trp Ser Tyr Ile Val Glu
530                 535                 540

Lys Ala Asn Pro Val Asn Asp Leu Cys Tyr Pro Gly Asp Phe Asn Asp
545                 550                 555                 560

Tyr Glu Glu Leu Lys His Leu Leu Ser Arg Ile Asn His Phe Glu Lys
                565                 570                 575

Ile Gln Ile Ile Pro Lys Ser Ser Trp Ser Ser His Glu Ala Ser Leu
            580                 585                 590

Gly Val Ser Ser Ala Cys Pro Tyr Gln Gly Lys Ser Ser Phe Phe Arg
        595                 600                 605

Asn Val Val Trp Leu Ile Lys Lys Asn Ser Thr Tyr Pro Thr Ile Lys
610                 615                 620

Arg Ser Tyr Asn Asn Thr Asn Gln Glu Asp Leu Leu Val Leu Trp Gly
625                 630                 635                 640

Ile His His Pro Asn Asp Ala Ala Glu Gln Thr Lys Leu Tyr Gln Asn
                645                 650                 655

Pro Thr Thr Tyr Ile Ser Val Gly Thr Ser Thr Leu Asn Gln Arg Leu
            660                 665                 670

Val Pro Arg Ile Ala Thr Arg Ser Lys Val Asn Gly Gln Ser Gly Arg
        675                 680                 685

Met Glu Phe Phe Trp Thr Ile Leu Lys Pro Asn Asp Ala Ile Asn Phe
690                 695                 700

Glu Ser Asn Gly Asn Phe Ile Ala Pro Glu Tyr Ala Tyr Lys Ile Val
705                 710                 715                 720

Lys Lys Gly Asp Ser Thr Ile Met Lys Ser Glu Leu Glu Tyr Gly Asn
                725                 730                 735

Cys Asn Thr Lys Cys Gln Thr Pro Met Gly Ala Ile Asn Ser Ser Met
            740                 745                 750

Pro Phe His Asn Ile His Pro Leu Thr Ile Gly Glu Cys Pro Lys Tyr
        755                 760                 765

Val Lys Ser Asn Arg Leu Val Leu Ala His His His His His His
770                 775                 780

<210> SEQ ID NO 10
<211> LENGTH: 524
<212> TYPE: PRT
<213> ORGANISM: Artificial
<220> FEATURE:
<223> OTHER INFORMATION: Chemically Synthesized Polypeptide

<400> SEQUENCE: 10

Glu Ile Gln Leu Gln Gln Thr Gly Pro Glu Leu Val Lys Pro Gly Ala
1               5                   10                  15

Ser Val Lys Ile Ser Cys Lys Ala Ser Gly Tyr Pro Phe Thr Asp Tyr

```
                    20                  25                  30
Ile Met Val Trp Val Lys Gln Ser His Gly Lys Ser Leu Glu Trp Ile
            35                  40                  45

Gly Asn Ile Ser Pro Tyr Tyr Gly Thr Thr Asn Tyr Asn Leu Lys Phe
        50                  55                  60

Lys Gly Lys Ala Thr Leu Thr Val Asp Lys Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Ser Pro Asn Trp Asp Gly Ala Trp Phe Ala His Trp Gly Gln
            100                 105                 110

Gly Ala Leu Val Thr Val Ser Ala Ala Lys Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys Ala
            435                 440                 445
```

Ser Asn Ser Pro Gln Asn Glu Val Leu Tyr Gly Asp Val Asn Asp Asp
            450                 455                 460

Gly Lys Val Asn Ser Thr Asp Leu Thr Leu Leu Lys Arg Tyr Val Leu
465                 470                 475                 480

Lys Ala Val Ser Thr Leu Pro Ser Ser Lys Ala Glu Lys Asn Ala Asp
                485                 490                 495

Val Asn Arg Asp Gly Arg Val Asn Ser Ser Asp Val Thr Ile Leu Ser
            500                 505                 510

Arg Tyr Leu Ile Arg Val Ile Glu Lys Leu Pro Ile
        515                 520

<210> SEQ ID NO 11
<211> LENGTH: 713
<212> TYPE: PRT
<213> ORGANISM: Artificial
<220> FEATURE:
<223> OTHER INFORMATION: Chemically Synthesized Polypeptide

<400> SEQUENCE: 11

Glu Ile Gln Leu Gln Gln Thr Gly Pro Glu Leu Val Lys Pro Gly Ala
1               5                   10                  15

Ser Val Lys Ile Ser Cys Lys Ala Ser Gly Tyr Pro Phe Thr Asp Tyr
            20                  25                  30

Ile Met Val Trp Val Lys Gln Ser His Gly Lys Ser Leu Glu Trp Ile
        35                  40                  45

Gly Asn Ile Ser Pro Tyr Tyr Gly Thr Thr Asn Tyr Asn Leu Lys Phe
    50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Ser Pro Asn Trp Asp Gly Ala Trp Phe Ala His Trp Gly Gln
            100                 105                 110

Gly Ala Leu Val Thr Val Ser Ala Ala Lys Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser

```
            290                 295                 300
Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys Ala
                435                 440                 445

Ser Asp Thr Thr Glu Pro Ala Thr Pro Thr Thr Pro Val Thr Thr Pro
450                 455                 460

Thr Thr Thr Leu Leu Ala Pro Leu Ile Leu Ser Arg Ile Val Gly Gly
465                 470                 475                 480

Trp Glu Cys Glu Lys His Ser Gln Pro Trp Gln Val Leu Val Ala Ser
                485                 490                 495

Arg Gly Arg Ala Val Cys Gly Gly Val Leu Val His Pro Gln Trp Val
                500                 505                 510

Leu Thr Ala Ala His Cys Ile Arg Asn Lys Ser Val Ile Leu Leu Gly
        515                 520                 525

Arg His Ser Leu Phe His Pro Glu Asp Thr Gly Gln Val Phe Gln Val
        530                 535                 540

Ser His Ser Phe Pro His Pro Leu Tyr Asp Met Ser Leu Leu Lys Asn
545                 550                 555                 560

Arg Phe Leu Arg Pro Gly Asp Asp Ser Ser His Asp Leu Met Leu Leu
                565                 570                 575

Arg Leu Ser Glu Pro Ala Glu Leu Thr Asp Ala Val Lys Val Met Asp
                580                 585                 590

Leu Pro Thr Gln Glu Pro Ala Leu Gly Thr Thr Cys Tyr Ala Ser Gly
            595                 600                 605

Trp Gly Ser Ile Glu Pro Glu Glu Phe Leu Thr Pro Lys Lys Leu Gln
        610                 615                 620

Cys Val Asp Leu His Val Ile Ser Asn Asp Val Cys Ala Gln Val His
625                 630                 635                 640

Pro Gln Lys Val Thr Lys Phe Met Leu Cys Ala Gly Arg Trp Thr Gly
                645                 650                 655

Gly Lys Ser Thr Cys Ser Gly Asp Ser Gly Gly Pro Leu Val Cys Asn
                660                 665                 670

Gly Val Leu Gln Gly Ile Thr Ser Trp Gly Ser Glu Pro Cys Ala Leu
            675                 680                 685

Pro Glu Arg Pro Ser Leu Tyr Thr Lys Val Val His Tyr Arg Lys Trp
        690                 695                 700

Ile Lys Asp Thr Ile Val Ala Asn Pro
705                 710
```

-continued

```
<210> SEQ ID NO 12
<211> LENGTH: 36
<212> TYPE: DNA
<213> ORGANISM: Artificial
<220> FEATURE:
<223> OTHER INFORMATION: Chemically Synthesized Oligonucleotide

<400> SEQUENCE: 12
ggatggtggg aagatggata cagttggtgc agcatc                                36

<210> SEQ ID NO 13
<211> LENGTH: 48
<212> TYPE: DNA
<213> ORGANISM: Artificial
<220> FEATURE:
<223> OTHER INFORMATION: Chemically Synthesized Oligonucleotide

<400> SEQUENCE: 13
ctaggaacag tcagcacggg acaaactctt ctccacagtg tgaccttc                   48

<210> SEQ ID NO 14
<211> LENGTH: 37
<212> TYPE: DNA
<213> ORGANISM: Artificial
<220> FEATURE:
<223> OTHER INFORMATION: Chemically Synthesized Oligonucleotide

<400> SEQUENCE: 14
gtcactggct cagggaaata gcccttgacc aggcatc                               37

<210> SEQ ID NO 15
<211> LENGTH: 31
<212> TYPE: DNA
<213> ORGANISM: Artificial
<220> FEATURE:
<223> OTHER INFORMATION: Chemically Synthesized Oligonucleotide

<400> SEQUENCE: 15
ccaggcatcc tagagtcacc gaggagccag t                                     31

<210> SEQ ID NO 16
<211> LENGTH: 38
<212> TYPE: DNA
<213> ORGANISM: Artificial
<220> FEATURE:
<223> OTHER INFORMATION: Chemically Synthesized Oligonucleotide

<400> SEQUENCE: 16
ggtgctggag gggacagtca ctgagctgct catagtgt                              38

<210> SEQ ID NO 17
<211> LENGTH: 107
<212> TYPE: DNA
<213> ORGANISM: Artificial
<220> FEATURE:
<223> OTHER INFORMATION: Chemically Synthesized Oligonucleotide

<400> SEQUENCE: 17
ctagttgctg gctaatggac cccaaaggct ccctttcctg gagaatactt ctgtttctct      60
ccctggcttt tgagttgtcg tacggattaa ttaagggccc actcgag                   107

<210> SEQ ID NO 18
<211> LENGTH: 100
<212> TYPE: DNA
<213> ORGANISM: Artificial
<220> FEATURE:
```

<223> OTHER INFORMATION: Chemically Synthesized Oligonucleotide

<400> SEQUENCE: 18
ctagttgctg gctaatggac cccaaaggct cccttcctg agaatactt ctgtttctct        60 ccctggcttt tgagttgtcg tacggattaa ttaagggccc        100

<210> SEQ ID NO 19
<211> LENGTH: 70
<212> TYPE: DNA
<213> ORGANISM: Artificial
<220> FEATURE:
<223> OTHER INFORMATION: Chemically Synthesized Oligonucleotide

<400> SEQUENCE: 19
gctagcgata caacagaacc tgcaacacct acaacacctg taacaacacc gacaacaaca        60
cttctagcgc        70

<210> SEQ ID NO 20
<211> LENGTH: 119
<212> TYPE: DNA
<213> ORGANISM: Artificial
<220> FEATURE:
<223> OTHER INFORMATION: Chemically Synthesized Oligonucleotide

<400> SEQUENCE: 20
gctagcccca ttctgagccc cctgaccaaa ggcattctgg ctttgtgtt taccctgacc        60 gtgcccagcg aacgcaaggg tatacttgga ttcgttttca cacttactta agcggccgc        119

<210> SEQ ID NO 21
<211> LENGTH: 273
<212> TYPE: PRT
<213> ORGANISM: artificial sequence
<220> FEATURE:
<223> OTHER INFORMATION: synthetic peptide

<400> SEQUENCE: 21

Met Thr Phe Asp Asp Leu Lys Ile Gln Thr Met Lys Asp Gln Pro Asp
1               5                   10                  15

Glu Lys Ser Asn Gly Lys Lys Ala Lys Gly Leu Gln Phe Leu Tyr Ser
            20                  25                  30

Pro Trp Trp Cys Leu Val Ala Val Thr Leu Ala Val Leu Cys Leu Gly
        35                  40                  45

Leu Gly Val Thr Ile Met Val Leu Gly Met Gln Leu Ser Gln Val Pro
    50                  55                  60

Asn Ile Leu Lys Gln Gln Gln Thr Asn Leu Thr His Gln Lys Asn Lys
65                  70                  75                  80

Leu Glu Gly Arg Ile Ser Ala Arg Gln Gln Ala Glu Glu Ala Ser Gln
                85                  90                  95

Glu Ser Gln Asn Glu Leu Lys Glu Met Ile Glu Thr Leu Ala Trp Lys
            100                 105                 110

Leu Asn Glu Lys Ser Lys Glu Gln Met Glu Leu His His Gln Asn Leu
        115                 120                 125

Asn Leu Gln Glu Thr Leu Lys Arg Val Ala Asn Cys Ser Ala Pro Cys
    130                 135                 140

Pro Gln Asp Trp Ile Trp His Glu Glu Asn Cys Tyr Leu Phe Ser Thr
145                 150                 155                 160

Gly Ser Phe Asn Trp Glu Lys Ser Gln Glu Lys Cys Leu Ser Leu Asp
                165                 170                 175

Ala Lys Leu Leu Lys Ile Asn Ser Thr Ala Asp Leu Asp Phe Ile Gln

```
                  180                 185                 190
Gln Ala Ile Ser Asp Ser Ser Phe Pro Phe Trp Met Gly Leu Ser Arg
            195                 200                 205
Arg Asn Pro Ser Tyr Pro Trp Leu Trp Glu Asp Gly Ser Pro Leu Met
        210                 215                 220
Pro His Leu Phe Arg Ile Arg Gly Ala Val Ser Gln Thr Tyr Pro Ser
225                 230                 235                 240
Gly Thr Cys Ala Tyr Ile Gln Arg Gly Ala Val Tyr Ala Glu Asn Cys
                245                 250                 255
Ile Leu Ala Ala Phe Ser Ile Cys Gln Lys Lys Ala Asn Leu Arg Ala
            260                 265                 270
Gln

<210> SEQ ID NO 22
<211> LENGTH: 273
<212> TYPE: PRT
<213> ORGANISM: artificial sequence
<220> FEATURE:
<223> OTHER INFORMATION: synthetic peptide

<400> SEQUENCE: 22

Met Thr Phe Asp Asp Leu Lys Ile Gln Thr Met Lys Asp Gln Pro Asp
1               5                   10                  15
Glu Lys Ser Asn Gly Lys Lys Ala Lys Gly Leu Gln Phe Leu Tyr Ser
            20                  25                  30
Pro Trp Trp Cys Leu Val Ala Val Thr Leu Ala Val Leu Cys Leu Gly
        35                  40                  45
Leu Gly Val Thr Ile Thr Val Leu Gly Met Gln Leu Ser Gln Val Ser
    50                  55                  60
Asn Ile Leu Lys Gln Gln Gln Thr Asn Leu Thr His Gln Lys Asn Lys
65              70                  75                  80
Leu Glu Gly Gln Ile Ser Ala Arg Gln Gln Ala Glu Glu Ala Ser Gln
                85                  90                  95
Glu Ser Gln Asn Glu Leu Lys Glu Met Ile Glu Thr Leu Ala Trp Lys
            100                 105                 110
Leu Asn Glu Lys Ser Lys Glu Gln Met Glu Leu His His Gln Asn Leu
        115                 120                 125
Asn Leu Gln Glu Thr Leu Lys Arg Val Ala Asn Cys Ser Ala Pro Cys
    130                 135                 140
Pro Gln Asp Trp Ile Trp His Glu Glu Asn Cys Tyr Leu Phe Ser Thr
145                 150                 155                 160
Gly Ser Phe Asn Trp Glu Lys Ser Gln Glu Lys Cys Leu Ser Leu Asp
                165                 170                 175
Ala Lys Leu Leu Lys Ile Asn Ser Thr Ala Asp Leu Asp Phe Ile Gln
            180                 185                 190
Gln Ala Ile Ser Tyr Ser Ser Phe Pro Phe Trp Met Gly Leu Ser Arg
        195                 200                 205
Arg Asn Pro Ser Tyr Pro Trp Leu Trp Glu Asp Gly Ser Pro Leu Met
    210                 215                 220
Pro His Leu Phe Arg Ile Arg Gly Ala Val Ser Gln Thr Tyr Pro Ser
225                 230                 235                 240
Gly Thr Cys Ala Tyr Ile Gln Arg Gly Ala Val Tyr Ala Glu Asn Cys
                245                 250                 255
Ile Leu Ala Ala Phe Ser Ile Cys Gln Lys Lys Ala Asn Leu Arg Ala
            260                 265                 270
```

Gln

```
<210> SEQ ID NO 23
<211> LENGTH: 273
<212> TYPE: PRT
<213> ORGANISM: artificial sequence
<220> FEATURE:
<223> OTHER INFORMATION: synthetic peptide
```

<400> SEQUENCE: 23

| Met | Thr | Phe | Asp | Asp | Leu | Lys | Ile | Gln | Thr | Met | Lys | Asp | Gln | Pro | Asp |
|---|---|---|---|---|---|---|---|---|---|---|---|---|---|---|---|
| 1 | | | | 5 | | | | | 10 | | | | | 15 | |

Glu Lys Ser Asn Gly Lys Lys Ala Lys Gly Leu Gln Phe Leu Tyr Ser
      20         25         30

Pro Trp Trp Cys Leu Val Ala Val Thr Leu Ala Val Leu Cys Leu Gly
     35         40         45

Leu Val Val Thr Ile Met Val Leu Gly Met Gln Leu Ser Gln Val Ser
    50         55         60

Asn Leu Leu Lys Gln Gln Gln Thr Asn Leu Thr His Gln Lys Asn Lys
65         70         75         80

Leu Glu Gly Gln Ile Ser Ala Arg Gln Gln Ala Glu Glu Ala Ser Gln
        85         90         95

Glu Ser Gln Asn Glu Leu Lys Glu Met Ile Glu Thr Leu Ala Trp Lys
      100        105         110

Leu Asn Glu Lys Ser Lys Glu Gln Met Glu Leu His His Gln Asn Leu
    115         120         125

Asn Leu Gln Glu Thr Leu Lys Arg Val Ala Asn Cys Ser Ala Pro Cys
  130         135         140

Pro Gln Asp Trp Ile Trp His Glu Gly Asn Cys Tyr Leu Phe Ser Thr
145         150         155         160

Gly Ser Phe Asn Trp Glu Lys Ser Gln Glu Lys Cys Leu Ser Leu Asp
      165        170         175

Ala Lys Leu Leu Lys Ile Asn Ser Thr Ala Asp Leu Asp Phe Ile Gln
    180         185         190

Gln Ala Ile Ser Tyr Ser Ser Phe Pro Phe Trp Met Gly Leu Ser Arg
        195         200         205

Arg Asn Pro Ser Tyr Pro Trp Leu Trp Glu Asp Gly Ser Pro Leu Met
  210         215         220

Pro His Leu Phe Arg Ile Arg Gly Ala Val Ser Gln Thr Tyr Pro Ser
225         230         235         240

Gly Thr Cys Ala Tyr Ile Gln Arg Gly Ala Val Tyr Ala Glu Asn Cys
        245         250         255

Ile Leu Ala Ala Phe Ser Ile Cys Gln Lys Lys Ala Asn Leu Arg Ala
    260         265         270

Gln

```
<210> SEQ ID NO 24
<211> LENGTH: 269
<212> TYPE: PRT
<213> ORGANISM: artificial sequence
<220> FEATURE:
<223> OTHER INFORMATION: synthetic peptide
```

<400> SEQUENCE: 24

Met Thr Phe Asp Asp Leu Lys Ile Gln Thr Met Lys Asp Gln Pro Asp
1         5         10         15

Glu Lys Ser Asn Gly Lys Lys Ala Lys Gly Leu Gln Phe Leu Tyr Ser
      20        25         30

```
Pro Trp Trp Cys Leu Val Ala Val Thr Leu Ala Val Leu Cys Leu Gly
        35              40                  45
Leu Val Val Thr Ile Met Val Leu Gly Met Gln Leu Ser Gln Val Ser
    50              55                  60
Asn Leu Leu Lys Gln Gln Thr Asn Leu Thr His Gln Lys Asn Lys
65              70              75                      80
Leu Glu Gly Gln Ile Ser Ala Arg Gln Gln Ala Glu Glu Ala Ser Gln
                85              90                  95
Glu Ser Gln Asn Glu Leu Lys Glu Met Ile Glu Thr Leu Ala Trp Lys
            100             105                 110
Leu Asn Glu Lys Ser Lys Glu Gln Met Glu Leu His His Gln Asn Leu
        115             120                 125
Asn Leu Gln Glu Thr Leu Lys Arg Val Ala Asn Cys Ser Ala Pro Cys
    130             135                 140
Pro Gln Asp Trp Ile Trp His Glu Gly Asn Cys Tyr Leu Phe Ser Thr
145             150                 155                 160
Gly Ser Phe Asn Trp Glu Lys Ser Gln Glu Lys Cys Leu Ser Leu Asp
                165                 170                 175
Ala Lys Ser Leu Lys Ile Asn Ser Thr Ala Asp Leu Asp Phe Ile Gln
            180                 185                 190
Gln Ala Ile Ser Tyr Ser Ser Phe Pro Phe Trp Met Gly Leu Ser Arg
        195                 200                 205
Arg Asn Pro Ser Tyr Pro Trp Leu Trp Glu Asp Gly Ser Pro Leu Met
    210             215                 220
Pro His Leu Phe Arg Ile Arg Gly Ala Val Ser Gln Thr Tyr Pro Ser
225             230                 235                 240
Gly Thr Cys Ala Tyr Ile Gln Arg Gly Ala Val Tyr Ala Glu Asn Cys
            245                 250                 255
Ile Leu Ala Ala Phe Ser Ile Cys Gln Lys Arg Gln Thr
            260             265
```